(12) United States Patent
Sanson et al.

(10) Patent No.: US 7,919,455 B2
(45) Date of Patent: Apr. 5, 2011

(54) MARKED PEPTIDES HAVING AFFINITY FOR A PHOSPHOLIPID AND USES

(75) Inventors: Alain Sanson, Gometz le Chatel (FR); Francoise Ochsenbein, Gif sur Yvette (FR); Frederic Dolle, Gometz le Chatel (FR)

(73) Assignees: Commissariat a l'Energie Atomique, Paris (FR); Universite Pierre et Marie Curie (Paris VI), Paris (FR)

( * ) Notice: Subject to any disclaimer, the term of this patent is extended or adjusted under 35 U.S.C. 154(b) by 570 days.

(21) Appl. No.: 10/518,382

(22) PCT Filed: Jun. 30, 2003

(86) PCT No.: PCT/FR03/02027
§ 371 (c)(1),
(2), (4) Date: Dec. 29, 2004

(87) PCT Pub. No.: WO2004/003016
PCT Pub. Date: Jan. 8, 2004

(65) Prior Publication Data
US 2006/0233706 A1     Oct. 19, 2006

(30) Foreign Application Priority Data

Jul. 1, 2002   (FR) ..................................... 02 08204

(51) Int. Cl.
*A61K 38/16* (2006.01)
(52) U.S. Cl. ............... 514/2; 514/12; 530/324; 548/548
(58) Field of Classification Search .................. None
See application file for complete search history.

(56) References Cited

U.S. PATENT DOCUMENTS 4,735,792 A    4/1988  Srivastava

FOREIGN PATENT DOCUMENTS

| EP | 0 293 567 | | 12/1988 |
|---|---|---|---|
| WO | 92/19279 | | 11/1992 |
| WO | WO 99/11590 | * | 3/1999 |
| WO | 00/20453 | | 4/2000 |

OTHER PUBLICATIONS

Zijlstra et al., "Synthesis and evaluation of a 18F-labelled recombinant annexin-V derivative, for identification and quantification of apoptotic cells with PET", Applied Radiation and Isotopes, vol. 58, No. 2, pp. 201-207. Feb. 2003.*

Montaville, Pierre et al. "A New Consensus Sequence for Phosphatidylserine Recognition by Annexins", Journal of Biological Chemistry, vol. 277, No. 27, pp. 24684-24693, XP002268388 2002.
Shiue, C.-Y. et al. "Synthesis of 18F-labelled N-(p-[18F]fluorophenyl)maleimide and Its Derivatives for Labelling Monoclonal Antibody with 18F", Journal of Labelled Compounds and Radiopharmaceuticals, vol. 26, pp. 287-289, XP002091356 1989.
Burgess, Kevin et al. "Solid-Phase Syntheses of Guanidines", Wiley-Interscience, pp. v-ix 2000.
Fliss, Henry et al. "Apoptosis in Ischemic and Reperfused Rat Myocardium", Circ. Res., vol. 79, pp. 949-956 1996.
Cordier-Ochsenbein, Francoise et al. "Exploring the Folding Pathways of Annexin I, a Multidomain Protein. II. Hierarchy in Domain Folding Propensities may Govern the Folding Process", J. Mol. Biol., vol. 279, pp. 1177-1185 1998.

* cited by examiner

*Primary Examiner* — Anish Gupta
(74) *Attorney, Agent, or Firm* — Oblon, Spivak, McClelland, Maier & Neustadt, L.L.P.

(57) ABSTRACT

The present invention relates to a peptide labelled with fluorine-18 for the specific recognition of lipid vectors. The peptide of the invention comprises the following peptide sequence (PI):

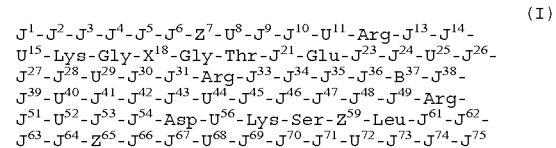

$$J^1-J^2-J^3-J^4-J^5-J^6-Z^7-U^8-J^9-J^{10}-U^{11}-Arg-J^{13}-J^{14}-U^{15}-Lys-Gly-X^{18}-Gly-Thr-J^{21}-Glu-J^{23}-J^{24}-U^{25}-J^{26}-J^{27}-J^{28}-U^{29}-J^{30}-J^{31}-Arg-J^{33}-J^{34}-J^{35}-J^{36}-B^{37}-J^{38}-J^{39}-U^{40}-J^{41}-J^{42}-J^{43}-U^{44}-J^{45}-J^{46}-J^{47}-J^{48}-J^{49}-Arg-J^{51}-U^{52}-J^{53}-J^{54}-Asp-U^{56}-Lys-Ser-Z^{59}-Leu-J^{61}-J^{62}-J^{63}-J^{64}-Z^{65}-J^{66}-J^{67}-U^{68}-J^{69}-J^{70}-J^{71}-U^{72}-J^{73}-J^{74}-J^{75}$$

in which the amino acids J are chosen independently of each other from natural amino acids, or derivatives thereof, in such a manner that at least 50% of them are polar residues chosen from Arg, Asn, Asp, Cys, Gln, Glu, Gly, His, Lys, Orn, Pro, Ser, Thr and Tyr, the amino acids U are chosen from Ala, Cys, Gly, Ile, Leu, Met, Phe, Trp, Tyr and Val, the amino acid $X^{18}$ is chosen independently of the other amino acids of the sequence from Ala, Asn, Cys, Gln, Gly, His, Ile, Leu, Met, Phe, Ser, Thr, Trp, Tyr and Val, the amino acid $B^{37}$ is chosen independently of the other amino acids of the sequence from Arg, Ala, Cys, Gly, Ile, Leu, Met, Phe, Trp, Tyr and Val, the amino acid $Z^7$ is chosen independently of the other amino acids from Asp and Glu, the amino acids $Z^{59}$ and $Z^{65}$ are chosen independently from Glu, Asp, Lys and Arg, the superscripts of the residues J, Z, U, X and B representing the positions of these amino acids in the said sequence.

18 Claims, 3 Drawing Sheets

AFIM-F
 A5-F
 H1

AFIM-F    H2    A5-F

SEQUENCE LISTING

<160> NUMBER OF SEQ ID NOS: 18

<210> SEQ ID NO 1
<211> LENGTH: 75
<212> TYPE: PRT
<213> ORGANISM: Artificial Sequence
<220> FEATURE:
<223> OTHER INFORMATION: Synthetic Peptide

<400> SEQUENCE: 1

```
Gly Phe Asp Glu Arg Ala Asp Val Glu Thr Leu Arg Lys Ala Met Lys
1               5                   10                  15

Gly Leu Gly Thr Asp Glu Glu Ser Ile Leu Thr Leu Leu Thr Ser Arg
            20                  25                  30

Ser Asn Ala Gln Arg Gln Glu Ile Ser Ala Ala Tyr Lys Thr Leu Phe
        35                  40                  45

Gly Arg Asp Leu Leu Asp Asp Leu Lys Ser Glu Leu Thr Gly Lys Phe
    50                  55                  60

Glu Lys Leu Val Val Ala Leu Leu Lys Pro Ser
65                  70                  75
```

<210> SEQ ID NO 2
<211> LENGTH: 75
<212> TYPE: PRT
<213> ORGANISM: Artificial Sequence
<220> FEATURE:
<223> OTHER INFORMATION: Synthetic Peptide

<400> SEQUENCE: 2

```
Asn Phe Asp Ala Glu Arg Asp Ala Leu Asn Ile Arg Lys Ala Ile Lys
1               5                   10                  15

Gly Met Gly Val Asp Glu Asp Thr Ile Val Asn Ile Leu Thr Asn Arg
            20                  25                  30

Ser Asn Ala Gln Arg Gln Asp Ile Ala Phe Ala Tyr Gln Arg Arg Thr
        35                  40                  45
```

```
Lys Arg Glu Leu Ala Ser Asp Leu Lys Ser Glu Leu Ser Gly His Leu
    50                  55                  60

Glu Arg Val Ile Leu Gly Leu Leu Lys Thr Ser
65                  70                  75

<210> SEQ ID NO 3
<211> LENGTH: 75
<212> TYPE: PRT
<213> ORGANISM: Artificial Sequence
<220> FEATURE:
<223> OTHER INFORMATION: Synthetic Peptide

<400> SEQUENCE: 3

Asp Phe Ser Pro Ser Val Asp Ala Glu Ala Ile Arg Lys Ala Ile Lys
1               5                   10                  15

Gly Ile Gly Thr Asp Glu Asp Met Leu Ile Ser Ile Leu Thr Glu Arg
                20                  25                  30

Ser Asn Ala Gln Arg Gln Leu Ile Val Lys Glu Tyr Gln Ala Ala Tyr
            35                  40                  45

Gly Arg Glu Leu Lys Asp Asp Leu Lys Ser Glu Leu Ser Gly His Phe
        50                  55                  60

Glu Arg Leu Met Val Ala Leu Val Thr Pro Ser
65                  70                  75

<210> SEQ ID NO 4
<211> LENGTH: 75
<212> TYPE: PRT
<213> ORGANISM: Artificial Sequence
<220> FEATURE:
<223> OTHER INFORMATION: Synthetic Peptide

<400> SEQUENCE: 4

Gly Phe Asn Ala Met Glu Asp Ala Gln Thr Leu Arg Lys Ala Met Lys
1               5                   10                  15

Gly Leu Gly Thr Asp Glu Asp Ala Ile Ile Ser Val Leu Ala Tyr Arg
                20                  25                  30

Asn Thr Ala Gln Arg Gln Glu Ile Arg Thr Ala Tyr Lys Ser Thr Ile
            35                  40                  45

Gly Arg Asp Leu Ile Asp Asp Leu Lys Ser Glu Leu Ser Gly Asn Phe
        50                  55                  60

Glu Arg Val Ile Val Gly Met Met Thr Pro Ser
65                  70                  75

<210> SEQ ID NO 5
<211> LENGTH: 75
<212> TYPE: PRT
<213> ORGANISM: Artificial Sequence
<220> FEATURE:
<223> OTHER INFORMATION: Synthetic Peptide

<400> SEQUENCE: 5

Gly Phe Asp Pro Asn Gln Asp Ala Glu Ala Leu Arg Thr Ala Met Lys
1               5                   10                  15

Gly Phe Gly Ser Asp Glu Glu Ala Ile Leu Asp Ile Ile Thr Ser Arg
                20                  25                  30

Ser Asn Arg Gln Arg Gln Glu Val Cys Gln Ser Tyr Lys Ser Leu Tyr
            35                  40                  45

Gly Arg Asp Leu Ile Ala Asp Leu Lys Ser Glu Leu Thr Gly Lys Phe
        50                  55                  60

Glu Arg Leu Ile Val Gly Leu Met Arg Pro Ser
```

-continued 65                70                75

<210> SEQ ID NO 6
<211> LENGTH: 75
<212> TYPE: PRT
<213> ORGANISM: Artificial Sequence
<220> FEATURE:
<223> OTHER INFORMATION: Synthetic Peptide

<400> SEQUENCE: 6

Gly Phe Asn Pro Asp Ala Asp Ala Lys Ala Leu Arg Lys Ala Met Lys
1               5                   10                  15

Gly Leu Gly Thr Asp Glu Asp Thr Ile Ile Asp Ile Ile Thr His Arg
            20                  25                  30

Ser Asn Val Gln Arg Gln Gln Ile Arg Gln Thr Phe Lys Ser His Phe
        35                  40                  45

Gly Arg Asp Leu Met Thr Asp Leu Lys Ser Glu Ile Ser Gly Asp Leu
    50                  55                  60

Glu Arg Leu Ile Leu Gly Leu Met Met Pro Ser
65                  70                  75

<210> SEQ ID NO 7
<211> LENGTH: 75
<212> TYPE: PRT
<213> ORGANISM: Artificial Sequence
<220> FEATURE:
<223> OTHER INFORMATION: Synthetic Peptide

<400> SEQUENCE: 7

Pro Gly Asp Ala Ile Arg Asp Ala Glu Ile Leu Arg Lys Ala Met Lys
1               5                   10                  15

Gly Phe Gly Thr Asp Glu Gln Ala Ile Val Asp Val Val Ala Asn Arg
            20                  25                  30

Ser Asn Asp Gln Arg Gln Lys Ile Lys Ala Ala Phe Lys Thr Ser Tyr
        35                  40                  45

Gly Arg Asp Leu Ile Lys Asp Leu Lys Ser Glu Leu Ser Gly Asn Met
    50                  55                  60

Glu Arg Leu Ile Leu Ala Leu Phe Met Pro Ser
65                  70                  75

<210> SEQ ID NO 8
<211> LENGTH: 75
<212> TYPE: PRT
<213> ORGANISM: Artificial Sequence
<220> FEATURE:
<223> OTHER INFORMATION: Synthetic Peptide

<400> SEQUENCE: 8

His Phe Asn Pro Asp Pro Asp Val Glu Thr Leu Arg Lys Ala Met Lys
1               5                   10                  15

Gly Ile Gly Thr Asn Glu Gln Ala Ile Ile Asp Val Leu Thr Lys Arg
            20                  25                  30

Ser Asn Thr Gln Arg Gln Thr Ile Ala Lys Ser Phe Lys Ala Gln Phe
        35                  40                  45

Gly Arg Asp Leu Thr Glu Asp Leu Lys Ser Glu Leu Ser Gly Lys Leu
    50                  55                  60

Glu Arg Leu Ile Val Ala Leu Met Tyr Pro Ser
65                  70                  75

<210> SEQ ID NO 9
<211> LENGTH: 75

```
<212> TYPE: PRT
<213> ORGANISM: Artificial Sequence
<220> FEATURE:
<223> OTHER INFORMATION: Synthetic Peptide

<400> SEQUENCE: 9

Gly Phe Asp Pro Leu Arg Asp Ala Glu Val Leu Arg Lys Ala Met Lys
1               5                   10                  15

Gly Phe Gly Thr Asp Glu Gln Ala Ile Ile Asp Cys Leu Gly Ser Arg
            20                  25                  30

Ser Asn Lys Gln Arg Gln Gln Ile Leu Leu Ser Phe Lys Thr Ala Tyr
        35                  40                  45

Gly Arg Asp Leu Ile Lys Asp Leu Lys Ser Glu Leu Ser Gly Asn Phe
    50                  55                  60

Glu Lys Thr Ile Leu Ala Leu Met Lys Thr Ser
65                  70                  75

<210> SEQ ID NO 10
<211> LENGTH: 75
<212> TYPE: PRT
<213> ORGANISM: Artificial Sequence
<220> FEATURE:
<223> OTHER INFORMATION: Synthetic Peptide

<400> SEQUENCE: 10

Gly Phe Asp Val Asp Arg Asp Ala Lys Lys Leu Arg Lys Ala Met Lys
1               5                   10                  15

Gly Met Gly Thr Asn Glu Ala Ala Ile Ile Glu Ile Leu Ser Gly Arg
            20                  25                  30

Thr Ser Asp Glu Arg Gln Gln Ile Lys Gln Lys Tyr Lys Ala Thr Tyr
        35                  40                  45

Gly Arg Glu Leu Glu Glu Asp Leu Lys Ser Glu Leu Ser Gly Asn Phe
    50                  55                  60

Glu Lys Thr Ala Leu Ala Leu Leu Asp Arg Ser
65                  70                  75

<210> SEQ ID NO 11
<211> LENGTH: 79
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (22)..(22)
<223> OTHER INFORMATION: Xaa = Leu, Met, or Trp
<220> FEATURE:
<221> NAME/KEY: MISC_FEATURE
<222> LOCATION: (34)..(34)
<223> OTHER INFORMATION: Xaa = Thr or Lys
<220> FEATURE:
<221> NAME/KEY: MISC_FEATURE
<222> LOCATION: (45)..(45)
<223> OTHER INFORMATION: Xaa = Ser or Lys
<220> FEATURE:
<221> NAME/KEY: MISC_FEATURE
<222> LOCATION: (48)..(48)
<223> OTHER INFORMATION: Xaa = Phe or Tyr
<220> FEATURE:
<221> NAME/KEY: MISC_FEATURE
<222> LOCATION: (50)..(50)
<223> OTHER INFORMATION: Xaa = Thr or Glu
<220> FEATURE:
<221> NAME/KEY: MISC_FEATURE
<222> LOCATION: (63)..(63)
<223> OTHER INFORMATION: Xaa = Gly or Lys
<220> FEATURE:
<221> NAME/KEY: MISC_FEATURE
```

```
<222> LOCATION: (69)..(69)
<223> OTHER INFORMATION: Xaa = Glu or Lys
<220> FEATURE:
<221> NAME/KEY: MISC_FEATURE
<222> LOCATION: (71)..(71)
<223> OTHER INFORMATION: Xaa = Glu or Leu

<400> SEQUENCE: 11

Gly Ser Gly Cys Gly Phe Asp Glu Arg Ala Asp Val Glu Thr Leu Arg
1               5                   10                  15

Lys Ala Met Lys Gly Xaa Gly Thr Asp Glu Glu Ser Ile Leu Thr Leu
            20                  25                  30

Leu Xaa Ser Arg Ser Asn Ala Gln Arg Gln Glu Ile Xaa Ala Ala Xaa
        35                  40                  45

Lys Xaa Leu Phe Gly Arg Asp Leu Leu Asp Asp Leu Lys Ser Xaa Leu
    50                  55                  60

Thr Gly Lys Phe Xaa Lys Xaa Val Val Ala Leu Leu Lys Pro Ser
65                  70                  75

<210> SEQ ID NO 12
<211> LENGTH: 78
<212> TYPE: PRT
<213> ORGANISM: Artificial Sequence
<220> FEATURE:
<223> OTHER INFORMATION: Synthetic Peptide

<400> SEQUENCE: 12

Gly Ser Pro Gly Phe Asp Glu Arg Ala Asp Val Glu Thr Leu Arg Lys
1               5                   10                  15

Ala Met Lys Gly Leu Gly Thr Asp Glu Glu Ser Ile Leu Thr Leu Leu
            20                  25                  30

Thr Ser Arg Ser Asn Ala Gln Arg Gln Glu Ile Ser Ala Ala Tyr Lys
        35                  40                  45

Thr Leu Phe Gly Arg Asp Leu Leu Asp Asp Leu Lys Ser Glu Leu Thr
    50                  55                  60

Gly Lys Phe Glu Lys Leu Val Val Ala Leu Leu Lys Pro Ser
65                  70                  75

<210> SEQ ID NO 13
<211> LENGTH: 83
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (25)..(25)
<223> OTHER INFORMATION: Xaa = Leu, Met, or Trp
<220> FEATURE:
<221> NAME/KEY: MISC_FEATURE
<222> LOCATION: (37)..(37)
<223> OTHER INFORMATION: Xaa = Thr or Lys
<220> FEATURE:
<221> NAME/KEY: MISC_FEATURE
<222> LOCATION: (48)..(48)
<223> OTHER INFORMATION: Xaa = Ser or Lys
<220> FEATURE:
<221> NAME/KEY: MISC_FEATURE
<222> LOCATION: (51)..(51)
<223> OTHER INFORMATION: Xaa = Phe or Tyr
<220> FEATURE:
<221> NAME/KEY: MISC_FEATURE
<222> LOCATION: (53)..(53)
<223> OTHER INFORMATION: Xaa = Thr or Glu
<220> FEATURE:
<221> NAME/KEY: MISC_FEATURE
<222> LOCATION: (66)..(66)
<223> OTHER INFORMATION: Xaa = Glu or Lys
```

```
<220> FEATURE:
<221> NAME/KEY: MISC_FEATURE
<222> LOCATION: (72)..(72)
<223> OTHER INFORMATION: Xaa = Glu or Lys
<220> FEATURE:
<221> NAME/KEY: MISC_FEATURE
<222> LOCATION: (74)..(74)
<223> OTHER INFORMATION: Xaa = Glu or Leu

<400> SEQUENCE: 13

Gly Ser Glu Cys Asp Phe Pro Gly Phe Asp Glu Arg Ala Asp Val Glu
1               5                   10                  15

Thr Leu Arg Lys Ala Met Lys Gly Xaa Gly Thr Asp Glu Glu Ser Ile
            20                  25                  30

Leu Thr Leu Leu Xaa Ser Arg Ser Asn Ala Gln Arg Gln Glu Ile Xaa
        35                  40                  45

Ala Ala Xaa Lys Xaa Leu Phe Gly Arg Asp Leu Leu Asp Asp Leu Lys
    50                  55                  60

Ser Xaa Leu Thr Gly Lys Phe Xaa Lys Xaa Val Val Ala Leu Leu Lys
65                  70                  75                  80

Pro Ser Arg

<210> SEQ ID NO 14
<211> LENGTH: 87
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (29)..(29)
<223> OTHER INFORMATION: Xaa = Leu, Met, or Trp
<220> FEATURE:
<221> NAME/KEY: MISC_FEATURE
<222> LOCATION: (41)..(41)
<223> OTHER INFORMATION: Xaa = Tyr or Lys
<220> FEATURE:
<221> NAME/KEY: MISC_FEATURE
<222> LOCATION: (52)..(52)
<223> OTHER INFORMATION: Xaa = Ser or Lys
<220> FEATURE:
<221> NAME/KEY: MISC_FEATURE
<222> LOCATION: (55)..(55)
<223> OTHER INFORMATION: Xaa = Phe or Tyr
<220> FEATURE:
<221> NAME/KEY: MISC_FEATURE
<222> LOCATION: (57)..(57)
<223> OTHER INFORMATION: Xaa = Thr or Glu
<220> FEATURE:
<221> NAME/KEY: MISC_FEATURE
<222> LOCATION: (70)..(70)
<223> OTHER INFORMATION: Xaa = Glu or Lys
<220> FEATURE:
<221> NAME/KEY: MISC_FEATURE
<222> LOCATION: (76)..(76)
<223> OTHER INFORMATION: Xaa = Glu or Lys
<220> FEATURE:
<221> NAME/KEY: MISC_FEATURE
<222> LOCATION: (78)..(78)
<223> OTHER INFORMATION: Xaa = Glu or Leu

<400> SEQUENCE: 14

Gly Ser Gly Cys Gly Thr Glu Thr Asp Phe Pro Gly Phe Asp Glu Arg
1               5                   10                  15

Ala Asp Val Glu Thr Leu Arg Lys Ala Met Lys Gly Xaa Gly Thr Asp
            20                  25                  30

Glu Glu Ser Ile Leu Thr Leu Leu Xaa Ser Arg Ser Asn Ala Gln Arg
        35                  40                  45

Gln Glu Ile Xaa Ala Ala Xaa Lys Xaa Leu Phe Gly Arg Asp Leu Leu
```

```
            50                  55                  60
Asp Asp Leu Lys Ser Xaa Leu Thr Gly Lys Phe Xaa Lys Xaa Val Val
 65                  70                  75                  80

Ala Leu Leu Lys Pro Ser Arg
             85

<210> SEQ ID NO 15
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 15

Gly Ser Gly Cys
1

<210> SEQ ID NO 16
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 16

Gly Cys Gly Ser
1

<210> SEQ ID NO 17
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 17

Gly Cys Gly Cys
1

<210> SEQ ID NO 18
<211> LENGTH: 75
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(6)
<223> OTHER INFORMATION: Xaa = any natural amino acid or amino acid
      derivative.
<220> FEATURE:
<221> NAME/KEY: MISC_FEATURE
<222> LOCATION: (8)..(8)
<223> OTHER INFORMATION: Xaa = Val or Ala
<220> FEATURE:
<221> NAME/KEY: MISC_FEATURE
<222> LOCATION: (9)..(10)
<223> OTHER INFORMATION: Xaa = any natural amino acid or amino acid
      derivative.
<220> FEATURE:
<221> NAME/KEY: MISC_FEATURE
<222> LOCATION: (11)..(11)
<223> OTHER INFORMATION: Xaa = Leu or Ile
<220> FEATURE:
<221> NAME/KEY: MISC_FEATURE
<222> LOCATION: (13)..(13)
<223> OTHER INFORMATION: Xaa = any natural amino acid or amino acid
      derivative.
<220> FEATURE:
<221> NAME/KEY: MISC_FEATURE
<222> LOCATION: (15)..(15)
```

```
<223> OTHER INFORMATION: Xaa = Met or Ile
<220> FEATURE:
<221> NAME/KEY: MISC_FEATURE
<222> LOCATION: (18)..(18)
<223> OTHER INFORMATION: Xaa = Ala, Asn, Cys, Gln, Gly, His, Ile, Leu,
      Met, Phe, Ser, Thr, Trp, Tyr or Val.
<220> FEATURE:
<221> NAME/KEY: MISC_FEATURE
<222> LOCATION: (21)..(21)
<223> OTHER INFORMATION: Xaa = any natural amino acid or amino acid
      derivative.
<220> FEATURE:
<221> NAME/KEY: MISC_FEATURE
<222> LOCATION: (23)..(24)
<223> OTHER INFORMATION: Xaa = any natural amino acid or amino acid
      derivative.
<220> FEATURE:
<221> NAME/KEY: MISC_FEATURE
<222> LOCATION: (25)..(25)
<223> OTHER INFORMATION: Xaa = Ile or Leu
<220> FEATURE:
<221> NAME/KEY: MISC_FEATURE
<222> LOCATION: (26)..(28)
<223> OTHER INFORMATION: Xaa = any natural amino acid or amino acid
      derivative.
<220> FEATURE:
<221> NAME/KEY: MISC_FEATURE
<222> LOCATION: (29)..(29)
<223> OTHER INFORMATION: Xaa = Leu, Ile, or Val
<220> FEATURE:
<221> NAME/KEY: MISC_FEATURE
<222> LOCATION: (30)..(31)
<223> OTHER INFORMATION: Xaa = any natural amino acid or amino acid
      derivative.
<220> FEATURE:
<221> NAME/KEY: MISC_FEATURE
<222> LOCATION: (33)..(36)
<223> OTHER INFORMATION: Xaa = any natural amino acid or amino acid
      derivative.
<220> FEATURE:
<221> NAME/KEY: MISC_FEATURE
<222> LOCATION: (37)..(37)
<223> OTHER INFORMATION: Xaa = Arg
<220> FEATURE:
<221> NAME/KEY: MISC_FEATURE
<222> LOCATION: (39)..(39)
<223> OTHER INFORMATION: Xaa = any natural amino acid or amino acid
      derivative.
<220> FEATURE:
<221> NAME/KEY: MISC_FEATURE
<222> LOCATION: (40)..(40)
<223> OTHER INFORMATION: Xaa = Ile or Val
<220> FEATURE:
<221> NAME/KEY: MISC_FEATURE
<222> LOCATION: (41)..(43)
<223> OTHER INFORMATION: Xaa = any natural amino acid or amino acid
      derivative.
<220> FEATURE:
<221> NAME/KEY: MISC_FEATURE
<222> LOCATION: (44)..(44)
<223> OTHER INFORMATION: Xaa = Tyr or Phe
<220> FEATURE:
<221> NAME/KEY: MISC_FEATURE
<222> LOCATION: (45)..(49)
<223> OTHER INFORMATION: Xaa = any natural amino acid or amino acid
      derivative.
<220> FEATURE:
<221> NAME/KEY: MISC_FEATURE
<222> LOCATION: (51)..(51)
<223> OTHER INFORMATION: Xaa = any natural amino acid or amino acid
      derivative.
<220> FEATURE:
<221> NAME/KEY: MISC_FEATURE
<222> LOCATION: (52)..(52)
<223> OTHER INFORMATION: Xaa = Leu
<220> FEATURE:
<221> NAME/KEY: MISC_FEATURE
<222> LOCATION: (53)..(54)
<223> OTHER INFORMATION: Xaa = any natural amino acid or amino acid
      derivative.
```

```
<220> FEATURE:
<221> NAME/KEY: MISC_FEATURE
<222> LOCATION: (56)..(56)
<223> OTHER INFORMATION: Xaa = Leu
<220> FEATURE:
<221> NAME/KEY: MISC_FEATURE
<222> LOCATION: (59)..(59)
<223> OTHER INFORMATION: Xaa = Glu, Asp, Lys, or Arg
<220> FEATURE:
<221> NAME/KEY: MISC_FEATURE
<222> LOCATION: (61)..(61)
<223> OTHER INFORMATION: Xaa = any natural amino acid or amino acid
      derivative.
<220> FEATURE:
<221> NAME/KEY: MISC_FEATURE
<222> LOCATION: (63)..(64)
<223> OTHER INFORMATION: Xaa = any natural amino acid or amino acid
      derivative.
<220> FEATURE:
<221> NAME/KEY: MISC_FEATURE
<222> LOCATION: (65)..(65)
<223> OTHER INFORMATION: Xaa = Glu, Asp, Lys, or Arg
<220> FEATURE:
<221> NAME/KEY: MISC_FEATURE
<222> LOCATION: (66)..(67)
<223> OTHER INFORMATION: Xaa = any natural amino acid or amino acid
      derivative.
<220> FEATURE:
<221> NAME/KEY: MISC_FEATURE
<222> LOCATION: (68)..(68)
<223> OTHER INFORMATION: Xaa = Val, Ile, Met, or Ala
<220> FEATURE:
<221> NAME/KEY: MISC_FEATURE
<222> LOCATION: (69)..(71)
<223> OTHER INFORMATION: Xaa = any natural amino acid or amino acid
      derivative.
<220> FEATURE:
<221> NAME/KEY: MISC_FEATURE
<222> LOCATION: (72)..(72)
<223> OTHER INFORMATION: Xaa = Leu, Val, Met, Phe or Ala
<220> FEATURE:
<221> NAME/KEY: MISC_FEATURE
<222> LOCATION: (73)..(74)
<223> OTHER INFORMATION: Xaa = any natural amino acid or amino acid
      derivative.
<220> FEATURE:
<221> NAME/KEY: MISC_FEATURE
<222> LOCATION: (1)..(75)
<223> OTHER INFORMATION: At least 50% of residues 1-6, 9, 10, 13, 14,
      21, 23, 24, 26-28, 30-31, 33-36, 38-39, 41-43, 45-49, 51, 53, 54,
      61-64, 66-67, 69-71 and 73-75 are polar residues chosen from Arg,
      Asn, Asp, Cys, Gln, Glu, Gly, His, Lys, Orn, Pro, Ser, Thr, or
      Tyr.

<400> SEQUENCE: 18

Xaa Xaa Xaa Xaa Xaa Xaa Asp Xaa Xaa Xaa Xaa Arg Xaa Ala Xaa Lys
1               5                   10                  15

Gly Xaa Gly Thr Xaa Glu Xaa Xaa Xaa Xaa Xaa Xaa Xaa Xaa Xaa Arg
            20                  25                  30

Xaa Xaa Xaa Xaa Xaa Gln Xaa Xaa Xaa Xaa Xaa Xaa Xaa Xaa Xaa Xaa
        35                  40                  45

Xaa Arg Xaa Xaa Xaa Xaa Asp Xaa Lys Ser Xaa Leu Xaa Gly Xaa Xaa
    50                  55                  60

Xaa Xaa Xaa Xaa Xaa Xaa Xaa Xaa Xaa Xaa Ser
65                  70                  75
```

MARKED PEPTIDES HAVING AFFINITY FOR A PHOSPHOLIPID AND USES

TECHNICAL FIELD

The present invention relates to a family of peptides labelled with fluorine-18 which have enhanced affinities for phospholipids, and to their uses.

In general, the peptides of the present invention are useful for the specific recognition of lipid molecules. They can be used for engineering and creating compounds recognizing and sequestering lipids, in particular negatively charged lipids, such as phosphatidylserines, phosphatidic and lysophosphatidic acids, phosphatidylglycerols, cardiolipins and sphingosine-1-phosphates.

The abovementioned lipids play an important role, in particular in cell signalling and may be present at the outer surface of cell membranes and/or circulate in the blood stream following a wide variety of pathological events.

Various cellular events result in the appearance of negatively charged lipids and in particular of phosphatidylserines (PS) at the outer surface of cells; these events can result either from a fortuitous or pathological impairment of the cell, or from a programmed cellular event such as cell death or apoptosis. The appearance of PS at the outer surface of cells therefore constitutes an important "primary message" indicating the existence of a dysfunction. In the case of the blood clotting process, the mechanism is well described: the impairment of the endothelial cells of the blood vessels, either for accidental reasons, or for more complex pathological reasons, causes the appearance of this PS message at the outer surface of the cells in contact with the blood stream. This message is immediately recognized by certain circulating proteins which then trigger a cascade of events resulting in the well-known phenomenon of blood clotting.

The invention exploits the property of the labelled peptides, which it provides, to bind, in the presence or absence of calcium, to lipids and in particular to those which are negatively charged, for the development of compounds which can be used as research and diagnostic tools in the field of the recognition of lipid effectors and of the detection of apoptosis, of blood clotting disorders, of septic shock and of acute inflammatory pathologies in particular.

The labelled peptides of the invention are coupled to a radioactive halogen, a positron emitter, which is fluorine $^{18}$F. With these labelled peptides, it is therefore possible, for example to detect apoptotic cells and to recognize negatively charged membrane microdomains.

They can be used for "in vitro" detection of pathologies involving the appearance of centres exposing negatively charged lipids at the surface of the cells and/or the release of microvesicles into the blood.

The labelled peptides of the present invention may also be used for the in vivo detection and the imaging of apoptotic foci, of thrombotic regions, and in general of centres exposing negatively charged lipids at the surface of cells and/or the release of microvesicles into the blood, for example by means of scintigraphic images, acquired by positron emission tomography (PET).

Other applications will also appear to persons skilled in the art on reading the description which follows.

STATE OF THE ART

A family of proteins, called annexins, have been described in the prior art as presenting a reversible functional anchor to the cell membrane, regulated by the calcium concentration and the presence of anionic phospholipids. Annexins constitute a family of proteins expressed in a wide variety of tissues, both in animals and in plants. It appears that they are not expressed either in bacteria or in yeast.

The structure of annexins comprises four domains of about 70 amino acids, or residues, with a very slight sequence homology, but with practically identical topology.

In the document WO 92/19279, J. TAIT describes conjugates having affinity for phospholipids. It describes in particular the use of an annexin, in particular of annexin V, to manufacture an active conjugate which can be used as thrombolytic agent.

Unfortunately, the compound described in this document and prepared from whole annexin by a method of genetic recombination has many disadvantages which are in particular a low yield and a high cost of manufacture. The major disadvantages are especially the production of a fragile conjugate because of its complex topology resulting in irreversible unfolding. In addition, these molecules exhibit a major toxicity for the kidney and the heart.

The present inventors have described, in application WO-A-00/20453, a first family of peptides overcoming the abovementioned disadvantages and exhibiting affinity for phospholipids and enhanced stability.

Moreover, it is known that for use in research and diagnosis, macromolecules, such as proteins or peptides, can be coupled to a labeling molecule allowing their detection, this labeling molecule may be for example a fluorescent molecule, gold particles, a paramagnetic compound or a molecule bearing a radioelement.

Proteins have been radioactively labelled with radioisotopes, iodine and various radioisotopes of metals, such as technetium, indium and gallium. More recently, proteins have been labelled with fluorine-18.

For example, peptides coupled to radioelements, such as fluorine, allow "in vivo" detection of the localization of thrombotic regions during all sorts of stroke, in particular of apoptotic and inflammatory foci, using imaging systems.

Thus, radioactive atoms which emit positrons having a short life span, and especially $^{18}$F, can in particular be detected by positron emission tomography (PET) apparatus.

Radioactive labeling with fluorine-18 poses, in particular because of the very short life span of fluorine-18 (close to 109.8 minutes), specific problems which are such that labeling with fluorine-18 is basically different from that with other halogens, such as iodine.

The abovementioned labeling may be carried out by any of the conventional techniques of organic chemistry known to persons skilled in the art, and by the synthesis of protein and peptide markers bearing one or more radioactive atoms with a short life span, in particular $^{18}$F. This marker generally consists, on the one hand, of a part capable of receiving, for example, an atom of $^{18}$F and, on the other hand, of a part containing any conventional functional group for linking to the macromolecule, for example to the protein.

These markers must satisfy the requirement for rapid and easy synthesis, because due to the short life span of radioisotopes such as $^{18}$F, the duration of synthesis should generally not exceed a few hours.

In addition, this synthesis, because of the high radioactivity of the compounds used, must be capable of being carried out by automated means.

Thus, the methods for labeling proteins or peptides with fluorine-18 involve markers also called labelled "conjugates" or "synthons", which are classified into three main families, depending on whether they react with the amine groups, the sulphydryl groups, or the carbohydrate groups of the macromolecules, such as proteins and peptides.

Among the compounds or conjugates reacting with amino groups, there may be mentioned imidates, such as 3-[$^{18}$F]fluoro-5-nitrobenzoimidate, which react, for example, with the $\epsilon$-NH$_2$ group of lysine in order to bind to a protein; activated esters, such as N-succinimidyl-[$^{18}$F]fluorobenzoate; carboxylic acids, such as N-(4-[$^{18}$F]fluorobenzoic) acid; aldehydes, such as 4-[$^{18}$F]pentafluorobenzaldehyde and isothiocyanates, such as 4-([$^{18}$F] fluoromethylphenylisothiocyanate).

Activated halides, such as (4-[$^{19}$F]fluorophenacyl)bromide, react with the amino groups, such as the $\epsilon$-NH$_2$ group of lysine and the —SH group of cysteine.

Amines, such as 1-(4-([$^{18}$F]fluoromethyl)benzoyl)aminobutane-4-amine, react with the CO$_2$H groups, for example of glutamic acid or of aspartic acid or with the CHO groups of glycoproteins.

Nitrenes with photochemical active centres, such as azidophenacyl [$^{18}$F]fluoride, also react with the amino groups, for example the $\epsilon$-NH$_2$ group of lysine.

The most effective and most widely described method for labeling proteins and peptides is that which uses activated acids, but it is also the method which exhibits the greatest nonspecificity because all the nucleophilic sites of the amino acids of the proteins or peptides will react with the labelled marker, conjugate or synthon.

Two methods which are more specific for labeling peptides and nucleotides exhibit good specificity toward the sulphur atoms, for example, of cysteine for peptides and for a phosphorothioate functional group for nucleotides.

They include, first of all, methods using haloacetamide "synthons" which, although satisfactory, have the disadvantage of being very slow and therefore not very suitable for $^{18}$F, because of its life span.

They then include methods using activated maleimides which can bind to the SH groups with a very good specificity because the reaction is very slow in relation, for example, to the $\epsilon$-NH$_2$ sites of lysine.

The reaction scheme involving the maleimido group is the following, in the case of a protein:

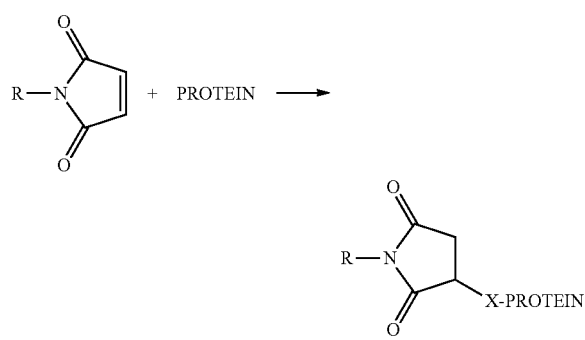

in which X represents —S—.

For any labeling, regardless of the type, molecules comprising a maleimide radical are currently considered as being the best, as regards their reactivity with macromolecules, such as peptides or proteins.

The document by SHIUE C.-Y. et al., J. Label Compounds Radiopharm 26: 278-280 (1988), describes the compounds:

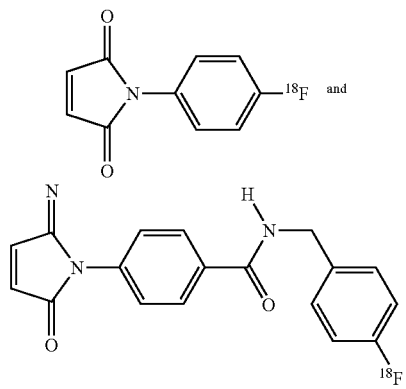

The first of these compounds is not easy to label with fluorine-18 at a high specific activity.

Indeed, only fluorine F$_2$ would allow easy labeling of the "iodine type" and it happens to be the case precisely that F$_2$ is generally a product with a low specific activity.

In particular F$_2$ is not suitable for the manufacture of so-called "radiotracer" compounds which are preferably aimed at according to the invention quite simply because the injected mass of labelled molecule becomes too large and in that case the basic principle guiding this "tracer", namely the extremely easy occupation (for example less than 5%) of the receptor sites, is not satisfied.

In addition, the synthesis of the first of these compounds is difficult; it is indeed carried out in four stages requiring a long period with very low yields, and relatively complex chemical conversions. This method cannot therefore be easily automated.

The second of the compounds cited in the SHIUE et al. document contains an amide chain which is not chemically very strong and which is easily cleaved or broken in vivo.

Its use for diagnostic applications cannot therefore be envisaged. In addition the synthesis of this second compound comprises three stages and the final yield is low, for example close to 10% ("EOB" "End of Bombardment").

The document U.S. Pat. No. 4,735,792 relates to molecules of formula:

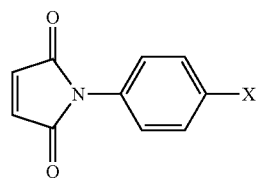

in which X is a radioactive halogen chosen from bromine-75, bromine-76, bromine-82, iodine-123, iodine-125, iodine-131 and fluorine-18.

However, only the molecule labelled with iodine-125 is effectively prepared.

The preparation of a molecule labelled with fluorine-18 is not mentioned or evoked, and the remarks already made above in the case of the first compound of the SHIUE et al., document also apply in the case of the document U.S. Pat. No. 4,735,792.

Persons skilled in the art, on reading this document, possess no information allowing them to specifically prepare a compound labelled with fluorine-18 and if they envisage doing it, they would use $F_2$ and would thus arrive at a compound with a low specific activity, which is unusable in "PET" imaging.

It can be considered additionally that the chemistry used to manufacture the fluorinated compound of the document U.S. Pat. No. 4,735,792 is a complex and long chemistry.

DISCLOSURE OF THE INVENTION

The aim of the present invention is precisely to provide a novel family of peptides, labelled with a radioactive halogen which is fluorine $^{18}F$ using a novel labeling compound, the peptide having affinity for lipids, in particular for phospholipids, more specific and further improved compared with the prior art products, and the labeling compound having, inter alia, high reactivity, high selectivity in particular towards sulphur atoms such as those of the thiol functional groups of cysteines, and a good specific activity and it being possible for the said labeling compound in addition to be manufactured by a method which is simple, reliable, easily automatible, rapid and of short duration.

The peptides of the invention have in addition the advantages of being chemically more stable than the prior art compounds and of being able to be manufactured reproducibly, with a high yield and a very low cost of production compared with the prior art compounds.

Fluorine-18 ($^{18}F$) is a positron emitter which allows detection, by means of the labelled peptides of the present invention, of negatively charged lipids in any region of the body by positron (PET) cameras. This coupling of the peptides of the present invention to $^{18}F$ makes it possible for example to detect, with a resolution better than the millimeter range, the presence of cells exhibiting phosphatidylserine (PS), present at the outer surface of the cells involved in physiopathological processes such as programmed cell death, apoptosis, blood clotting, inflammatory reaction in vivo in any living being. It also allows such a detection in vitro in laboratory tests.

These labelled peptides of the present invention also make it possible to precisely quantify for example the number of cells having phosphatidylserine.

The peptides of the present invention are characterized in that they comprise the following peptide sequence (PI):

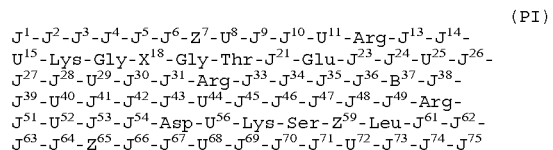

in which J, Z, U, X and B represent amino acids such that:
  the amino acids J are chosen independently of each other from natural amino acids, or derivatives thereof, in such a manner that at least 50% of them are polar residues chosen from Arg, Asn, Asp, Cys, Gln, Glu, Gly, His, Lys, Orn, Pro, Ser, Thr and Tyr,
  the amino acids U are chosen from Ala, Cys, Gly, Ile, Leu, Met, Phe, Trp, Tyr and Val,
  the amino acid $X^{18}$ is chosen independently of the other amino acids of the sequence from Ala, Asn, Cys, Gln, Gly, His, Ile, Leu, Met, Phe, Ser, Thr, Trp, Tyr and Val,
  the amino acid $B^{37}$ is chosen independently of the other amino acids of the sequence from Arg, Ala, Cys, Gly, Ile, Leu, Met, Phe, Trp, Tyr and Val, the amino acid $Z^7$ is chosen independently of the other amino acids of the sequence from Asp and Glu,
  the amino acids $Z^{59}$ and $Z^{65}$ are chosen independently from Glu, Asp, Lys and Arg,
  the superscripts of J, Z, U, X and B representing the positions of these amino acids in the said sequence.

According to the invention, these peptides of the present invention, as defined above, are labelled directly or indirectly with a labeling compound of the present invention of the following general formula (CI):

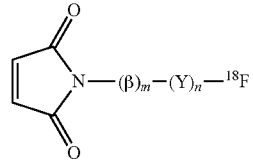

in which:
  m represents an integer from 0 to 10, such as 0, 1, 2, 3, 4, 5, 6, 7, 8, 9 or 10;
  n represents an integer from 0 to 10, such as 0, 1, 2, 3, 4, 5, 6, 7, 8, 9 or 10;
  Y represents a group chosen from alkyl groups, monocyclic or bicyclic heterocyclic groups chosen from imidazolyl, pyrazolyl, benzimidazolyl, pyridinyl, piridazinyl, pyrimidinyl, pyrazinyl, triazinyl, quinolinyl, isoquinolinyl, cinnolinyl, quinazolinyl, quinoxalinyl and purinyl groups, it being possible for Y to be optionally substituted with one or more substituents, each of these substituents being chosen independently from hydrogen, (nonradioactive) halogens, phenyl, $C_{1-6}$ alkyl, $C_{1-6}$ alkoxy, aryloxy, amino, mono- or di($C_{1-6}$ alkyl)amino, mono- or di(aryl)amino, thio, $C_{1-6}$ alkylthio, arylthio, formyl, $C_{1-6}$ alkylcarbonyl, arylcarbonyl, carbonyl, $C_{1-6}$ alkoxycarbonyl, aryloxycarbonyl, $C_{1-6}$ alkylaminocarbony arylaminocarbonyl and trifluoromethyl groups;
  β represents a radical of formula:

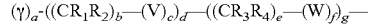

in which:
  a, b, c, d, e, f, g each independently represent an integer from 0 to 10, such as 0, 1, 2, 3, 4, 5, 6, 7, 8, 9;
  γ, V and W each independently represent —NR—$_1$, —O—, —S—,

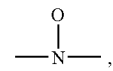

ethynyl, —$CR_1$=$CR_2$—, —(C=O)—, —(C=S)—, —C(=$NR_1$)—, —C(=O)O—, —(C=S)S—, —C(=$NR_1$)$NR_2$—, —$CR_1R_2$—, —$CR_1OR_2$—, —$CR_1NR_2R_3$—, where $R_1$, $R_2$: $R_3$ and $R_4$ are independently chosen from hydrogen, halogens, phenyl, $C_{1-6}$ alkyl, $C_{1-6}$ alkoxy, aryloxy, amino, mono- or di($C_{1-6}$ alkyl)amino, mono- or di(aryl)amino, thio, $C_{1-6}$ alkylthio, arylthio, formyl, $C_{1-6}$ alkylcarbonyl, arylcarbonyl, carbonyl ($C_{1-6}$)alkoxycarbonyl, aryloxycarbonyl, $C_{1-6}$ alkylaminocarbonyl, arylaminocarbonyl and trifluoromethyl groups.

Generally, in the present description, halogen means fluorine, chlorine, bromine or iodine. $C_{1-6}$ alkyl corresponds to linear and branched chain saturated hydrocarbon radicals having from 1 to 6 carbon atoms, such as methyl, ethyl, propyl, butyl, pentyl and hexyl.

The attachment and the substitution of the heterocycles, aryl group, and the like, may be made in any position.

Likewise, the attachment of the $^{18}F$ to Y or β may be made in any position, in particular to any position on a heterocycle.

The compounds according to the present invention are basically distinguishable from the prior art compounds because of their specific structure in which the part bearing the fluorine-18 atom consists, according to the invention, of a specific group Y which is in particular a pyridinyl group; the part for linking, coupling to the peptide consists, according to the invention, of a specific functional group, namely a maleimido functional group; and, finally, the part for binding to the peptide and the part bearing the fluorine-18 atom are linked according to the invention by a spacer chain or arm which is also specific, for example of the type comprising alkyl (generally from 2 to 6C), alkyl ether, phenylalkyl ethers, alkenyl, which are not fragile and are not susceptible to breakings "in vivo".

The expression direct labeling is understood to mean a direct coupling, without intermediate, such as a spacer arm, of the labeling compound (CI) with the peptide of the present invention, for example by means of a free —SH functional group of the peptide defined above; this may be in particular the thiol functional group of a cysteine of the peptide.

This coupling of the labeling compound (CI) with the peptide can be carried out either on the sequence (PI) defined above, for example on cysteine residues localized at the surface of the protein, but in a manner which is not disruptive for the functional groups for binding calcium and phospholipids, or on a portion of the peptide other than that of the said sequence (PI). The coupling occurs through the maleimide functional group of the compound (CI).

More precisely, the said coupling is achieved by the reaction of the double bond of the maleimido group of the compound according to the invention with specifically an —SH (thiol) functional group of a cysteine forming part of the peptide.

One of the advantages linked to the specific structure of the compounds according to the invention is to allow specific, or even exclusive, labeling of the cysteines, whereas most of the other "synthons" only allow nonspecific labeling of the lysines and of the cysteines.

The selective, or even exclusive, labeling of the cysteines is due to the presence, in the labeling molecule of the invention, of a "dedicated" functional group, namely the maleimido functional group, which is a dedicated functional group for the chemoselectivity towards the thiols of the cysteines.

The expression indirect labeling is understood to mean the use of a spacer arm linked, on the one hand, to the labeling compound, and, on the other hand, to the peptide as defined above. This spacer arm may have the role of putting the marker and the peptide apart so that no steric hindrance prevents the peptide from recognizing its target (negatively charged lipid). This spacer arm may be of an organic nature, for example an alkyl provided with a thiol group, or a peptide sequence comprising a cysteine, for example -(Gly)$_n$-Cys where n is equal to or greater than 1.

It is evident that the coupling of the labeling compound with the peptide in accordance with the present invention will be in any case such that it does not inhibit or inhibits in a manner which is not very disruptive the activity for the specific recognition of the negatively charged lipids by the peptide of the present invention.

The above peptide sequence (PI) falls in space in order to adopt its tertiary conformation which is the active form of the peptide.

The amino acids 12, 15, 16, 17, 19, 20, 22, 50, 55, 57, 58, 59, 60 and 65 of the peptide (PI) of the present invention are amino acids, or residues, involved directly or indirectly in the binding to lipids, that is to say that they are involved either in the three-dimensional structure of the peptide so that it adopts its active conformation for recognition, or in the site for recognition of the lipid.

The amino acids J are the surface amino acids or residues of this peptide when it is in its folded and active conformation. These residues are arranged in space such that they are partially or completely exposed to the solvent. According to the present invention, these amino acids J may for example be chosen independently of each other from all the natural amino acid residues Ala, Arg, Asn, Asp, Cys, Gln, Glu, Gly, His, Ile, Leu, Lys, Met, Orn, Phe, Pro, Ser, Thr, Trp, Tyr, and Val: and in such a manner that at least 50% of them are polar residues chosen from Arg, Asn, Asp, Cys, Gln, Glu, Gly, His, Lys, Orn, Pro, Ser and Thr. Examples are given in the appended sequence listing.

The amino acids U are the core residues of this peptide. In the folded and active conformation of the peptide, they are arranged in space close to each other and not exposed to the solvent. They constitute the hydrophobic core of the protein. The compact assembly of the atoms of these residues plays a predominant role for the stability of the peptide in its active conformation. These residues may be chosen from the list of amino acids U described above. Various examples of combinations of core residues in the peptide sequence (PI) of the present invention are given in the table (1) below:

TABLE 1

|  | $U^8$ | $U^{11}$ | $U^{15}$ | $U^{25}$ | $U^{29}$ | $B^{37}$ | $U^{40}$ | $U^{44}$ | $U^{52}$ | $U^{56}$ | $U^{68}$ | $U^{72}$ |
|---|---|---|---|---|---|---|---|---|---|---|---|---|
| Ex a) | Val | Leu | Met | Ile | Leu | Arg | Ile | Tyr | Leu | Leu | Val | Leu |
| Ex b) | Ala | Ile | Ile | Ile | Leu | Arg | Ile | Tyr | Leu | Leu | Ile | Leu |
| Ex c) | Ala | Ile | Ile | Ile | Leu | Arg | Ile | Tyr | Leu | Leu | Met | Val |
| Ex d) | Ala | Leu | Met | Leu | Leu | Arg | Ile | Tyr | Leu | Leu | Ile | Met |
| Ex e) | Ala | Leu | Met | Ile | Ile | Arg | Val | Tyr | Leu | Leu | Ile | Met |
| Ex f) | Ala | Leu | Met | Ile | Ile | Arg | Ile | Phe | Leu | Leu | Ile | Met |
| Ex g) | Ala | Leu | Met | Ile | Val | Arg | Ile | Phe | Leu | Leu | Ile | Phe |
| Ex h) | Val | Leu | Met | Ile | Leu | Arg | Ile | Phe | Leu | Leu | Ile | Met |
| Ex i) | Ala | Leu | Met | Ile | Leu | Arg | Ile | Phe | Leu | Leu | Ile | Met |
| Ex j) | Ala | Leu | Met | Ile | Leu | Arg | Ile | Tyr | Leu | Leu | Ala | Ala |
| Ex k) | Val | Leu | Met | Ile | Leu | Arg | Ile | Tyr | Leu | Leu | Val | Leu |
| Ex l) | Val | Leu | Met | Ile | Leu | Arg | Ile | Phe | Leu | Leu | Val | Leu |

(Ex = exemple)

(Ex=Example)

The residue $X^{18}$ has the role of maintaining the structure of the Gly-X-Gly loop in the active form of the peptide, in particular where the residues $Z^{59}$ and $Z^{65}$ are Glu, to modulate the hydrophobic and lipophilic character of this loop, and to optionally provide specific novel interactions with phospholipids. That is the case for example for the residues Asn, Cys, Ser, Thr, Trp and Tyr.

The residues $Z^{59}$ and $Z^{65}$ may be advantageously lysine residues, which has the effect of replacing the calcium ion with the positively charged group $—NH_3^+$ of the lysine and of enhancing the affinity of the peptide for a negatively charged membrane.

The peptide (PI) of the present invention, in its active form, comprises three sites for binding to a calcium ion where the calcium ion complexed by this site constitutes one of the ligands of a negatively charged phospholipid. The first of these sites, called principal site, involves the residues 15, 18, 19 and 59 as calcium ligands. The second of these sites, called secondary site, involves the residues 20 and 22 as calcium ligands. The third of these sites, which is a secondary site of low affinity involves the residues 57, 60 and 65 as calcium ligands.

The residues which are involved overall in the binding to the phospholipids are the residues 12, 15, 16, 19, 20, 22, 50, 55, 57, 58, 59, 60 and 65. This list includes residues involved in the bindings of calcium, the phospholipids being calcium ligands.

These residues may of course be replaced by residues playing the same role for the purpose of the same result in accordance with the present invention.

By way of example, according to the invention, the peptide of formula (PI) may be advantageously a peptide sequence chosen from the appended peptide sequences ID No. 1 to ID No. 10.

The sequence (PI) represents the peptides of the present invention in their shortest functional form. It is of course understood that this sequence may additionally comprise, linked to the N-terminal end and/or to the C-terminal end of the sequence (PI), one or more amino acids, for example from 1 to 15 amino acids, in general from 1 to 10 amino acids. Most preferably, these additional amino acids do not modify or only slightly modify the activity of the peptides, or else enhance it.

For example, a small sequence, called below functionalization sequence may be useful in particular for attaching a marker to the peptide, for attaching a molecule for treating diseases to the peptide and/or for attaching the said peptide to a support. The length of this functionalization sequence may be adapted according to its use. Of course, the latter will preferably not interfere with the activity of the peptide of the present invention. Persons skilled in the art will easily know how to adapt the length and the nature of this functionalization sequence according to the use that will be made of a peptide of the present invention.

Thus, according to a first particular embodiment of the present invention, the peptides of the present invention may contain, for example at the N-terminal end, a functionalization sequence of three amino acids. This functionalization sequence allows direct attachment of the labeling compound (CI) to the peptide. The peptides in accordance with this embodiment may be defined by the following sequence (PII):

(PII)

$J^{-2}$-$J^{-1}$-$J^{0}$-$J^{1}$-$J^{2}$-$J^{3}$-$J^{4}$-$J^{5}$-$J^{6}$-$Z^{7}$-$U^{8}$-$J^{9}$-$J^{10}$-$U^{11}$-Arg-
$J^{13}$-$J^{14}$-$U^{15}$-Lys-Gly-$X^{18}$-Gly-Thr-$J^{21}$-Glu-$J^{23}$-$J^{24}$-
$U^{25}$-$J^{26}$-$J^{27}$-$J^{28}$-$U^{29}$-$J^{30}$-$J^{31}$-Arg-$J^{33}$-$J^{34}$-$J^{35}$-$J^{36}$-
$B^{37}$-$J^{38}$-$J^{39}$-$U^{40}$-$J^{41}$-$J^{42}$-$J^{43}$-$U^{44}$-$J^{45}$-$J^{46}$-$J^{47}$-$J^{48}$-

-continued $J^{49}$-Arg-$J^{51}$-$U^{52}$-$J^{53}$-$J^{54}$-Asp-$U^{56}$-Lys-Ser-$Z^{59}$-Leu-
$J^{61}$-$J^{62}$-$J^{63}$-$J^{64}$-$Z^{65}$-$J^{66}$-$J^{67}$-$U^{68}$-$J^{69}$-$J^{70}$-$J^{71}$-$U^{72}$-
$J^{73}$-$J^{74}$-$J^{75}$ in which J, Z, U, X and B are as defined above.

For example, $J^{-2}$ may be Gly, $J^{-1}$ may be Ser or Cys and $J^0$ may be Cys, Thr, Pro, Ser or Gln, preferably $J^0$ is Cys.

This sequence $J^{-2}J^{-1}$-$J^0$ may be chosen for example from Gly-Ser-Cys-, and Gly-Cys-Ser-. Thus, for example, each of the sequences ID No. 1 to ID No. 10 mentioned above may contain according to choice each of the abovementioned functional sequences. The sequence ID No. 12 of the appended sequence listing is only a nonlimiting example of a sequence (PII) according to the present invention containing at its N-terminal end a functional sequence of three amino acids.

According to a second particular embodiment of the present invention, the peptide sequence (PI) may contain, for example at their N-terminal end, a functionalization sequence of four amino acids $J^{-3}$-$J^{-2}J^{-1}$-$J^0$ chosen from Gly-Ser-Gly-Cys-, Gly-Cys-Gly-Ser, and Gly-Cys-Gly-Cys. This functionalization sequence is useful for example for direct attachment of the labeling compound (CI) to the peptide. Thus, for example, each of the abovementioned sequences ID No. 1 to ID No. 10 may contain according to choice each of the abovementioned functional sequences. The sequences ID No. 11 of the appended sequence listing (several sequences are grouped under a single name ID No. 11) are only nonlimiting examples of sequences (PI) according to the present invention containing at its N-terminal end a functional sequence of four amino acids.

According to a third particular embodiment of the present invention, the peptide sequences (PI) may contain, for example at their N-terminal end, a functionalization sequence of seven to eleven amino acids. This functionalization sequence is also useful for directly attaching the compound (CI) to the peptide. This embodiment is set out below. Thus, for example, each of the sequences ID No. 1 to ID No. 10 mentioned above may contain according to choice each of the abovementioned functional sequences. It is also possible to replace the sequence Gly-Ser-Gly-Cys of the sequences ID No. 11 to 14 by Gly-Bb1-Gly-Bb2, in which Bb1 and Bb2 are independently Cys or Ser. The sequences ID No. 13 and 14 of the appended sequence listing (several sequences are grouped into one under the name ID No. 13 or 14) are merely nonlimiting examples of such peptides.

The peptides of the present invention have a sufficient affinity for calcium and are capable of reversibly binding to lipid effectors, and in particular to those which are negatively charged, such as phosphatidylserines, phosphatidic acids, phosphatidylethanolamines, phosphatidylglycerols, cardiolipins and phosphatidylinositolphosphates.

This is a family of peptides whose main property is to specifically recognize the appearance of lipid signals at the surface of cell membranes in relation to the normal or pathological function of the tissues.

The peptides of the present invention may be synthesized by conventional methods of organic chemistry synthesis or of protein chemistry, and by genetic recombination in vivo or in vitro, by genetic engineering, and the like.

The peptide according to the invention may be synthesized by solid-phase chemical synthesis of the said peptide. This chemical synthesis may be carried out for example with an automatic peptide synthesizer of the Applied Biosystems, mod. 433A type. It may be carried out for example by Fmoc chemistry which uses the fluorenylmethyloxycarbonyl group for the temporary protection of the α-amino functional group of amino acids.

The technical elements for the implementation of this method of peptide synthesis are known to persons skilled in the art. They are described for example in the manual Solid-Phase Organic Synthesis by Kevin Burgess (Editor) Wiley-Interscience; ISBN: 0471318256; (February 2000).

The peptide of the invention may also be manufactured by genetic recombination in vivo for example by means of a method comprising the following steps:
a) preparation of a cDNA comprising a basic sequence encoding the said peptide
b) insertion of the said cDNA into an appropriate expression vector,
c) transformation of an appropriate host cell with the said vector into which the cDNA has been inserted, for replication of the plasmid,
d) manufacture of the said peptide by translation of the said cDNA in the said host cell, and
e) recovery of the peptide synthesized.

According to the invention, the appropriate expression vector and the host cell are chosen according to the usual techniques for genetic recombination. The vector may be any of the plasmids generally used in this technique, for example a plasmid such as the vector pGEX-2T. Likewise, the cell may be chosen according to the usual techniques; it may be for example *E. coli*.

When a genetic recombination technique in vitro is used, steps c) and d) of the above method are replaced respectively by steps c') for introducing the vector into which the cDNA has been inserted in a suitable reaction medium for replication of the plasmid, and d') for manufacture of the said peptide by translation of the said cDNA in the said suitable reaction medium. The document Jagus, R. and Beckler, G. S. (1998) Overview of eukaryotic in vitro translation and expression systems, *Current Protocols in Cell Biology* 11.1.1-11.1.13., 1998 by John Wiley & Sons, Inc. describes methods in vitro which can be used in the present invention.

According to the invention, advantageously, in the above labeling compound (CI), n=1, and Y is a 3-pyridinyl group.

The compounds of formula (CI) may belong to various families, a first family may be defined as that of the "alkyl ethers", which correspond to the following formula (CII):

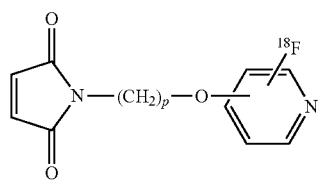
(CII)

in which p is an integer from 1 to 10, such as 2, 3, 4, 5, 6, 7, 8 or 9.

The preferred compounds of formula (CII) are chosen from the following compounds:

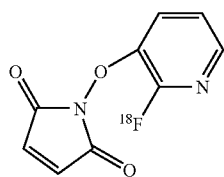

1-[(2-[$^{18}$F]fluoropyridin-3-yloxy)methyl]pyrrole-2,5-dione

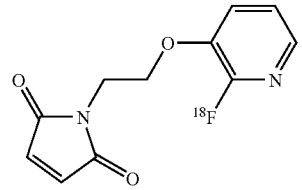

1-[2-(2-[$^{18}$F]fluoropyridin-3-yloxy)ethyl]pyrrole-2,5-dione

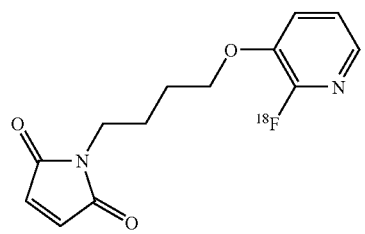

1-[4-(2-[$^{18}$F]fluoropyridin-3-yloxy)butyl]pyrrole-2,5-dione

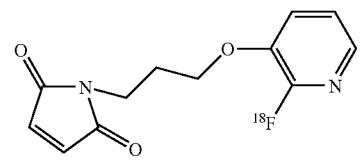

1-[3-(2-[$^{18}$F]fluoropyridin-3-yloxy)propyl]pyrrole-2,5-dione

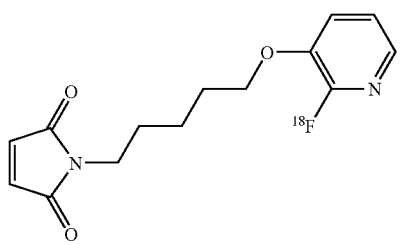

1-[5-(2-[$^{18}$F]fluoropyridin-3-yloxy)pentyl]pyrrole-2,5-dione

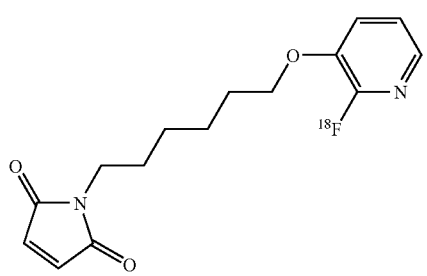

1-[6-(2-[$^{18}$F]fluoropyridin-3-yloxy)hexyl]pyrrole-2,5-dione

A second family of compounds of formula (CI) may be defined as those of the "phenylalkyl ethers", which correspond to the following formula (CIII):

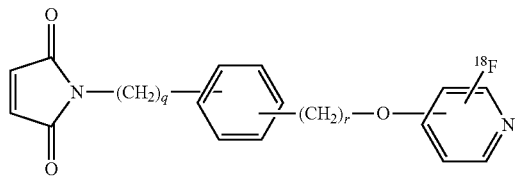

(CIII)

in which q and r represent independently an integer from 0 to 10, such as 0, 1, 2, 3, 4, 5, 6, 7, 8, 9.

The preferred compounds of formula (CIII) are chosen from the following compounds:

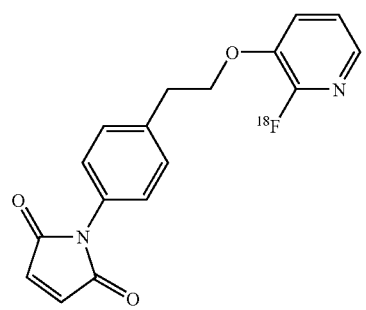

1-{4-[2-(2-[$^{18}$F]fluoropyridin-3-yloxy)ethyl]phenyl}pyrrole-2,5-dione

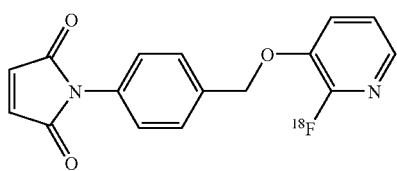

1-[4-(2-[$^{18}$F]fluoropyridin-3-yloxymethyl)phenyl]pyrrole-2,5-dione

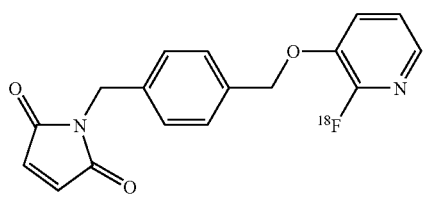

1-[4-(2-[$^{18}$F]fluoropyridin-3-yloxymethyl)benzyl]pyrrole-2,5-dione

A third family is that of the compounds which correspond to the following formula (CIV):

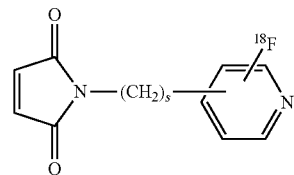

(CIV)

in which s is an integer from 1 to 10, such as 2, 3, 4, 5, 6, 7, 8, 9.

A preferred compound of formula (CIV) is the following compound:

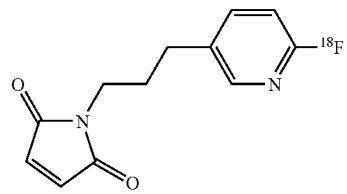

1-[3-(6-[$^{18}$F]fluoropyridin-3-yl)propyl]pyrrole-2,5-dione

A fourth family is that of the compounds which correspond to the following formula (CV):

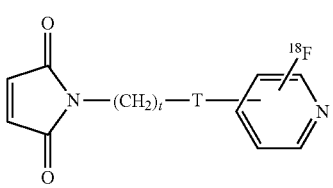

(CV)

in which t is an integer from 0 to 10, such as 1, 2, 3, 4, 5, 6, 7, 8, 9 and T is a group —CH═CH— or —C≡C—.

Preferred compounds of formula (CV) are the following compounds:

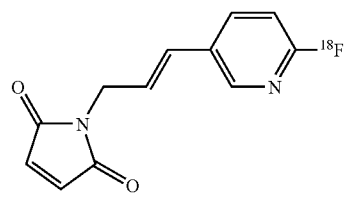

1-[3-(6-[$^{18}$F]fluoropyridin-3-yl)allyl]pyrrole-2,5-dione

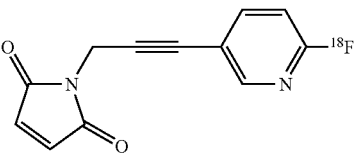

1-[3-(6-[$^{18}$F]fluoropyridin-3-yl)prop-2-ynyl]pyrrole-2,5-dione

The labeling compound (CI) may be prepared by a method in which:

a) a precursor compound of formula (CIa):

$$PR_1-\underset{\underset{PR_2}{|}}{N}-(\beta)_m-(Y)_n-Gp \quad (CIa)$$

in which $PR_1$ and $PR_2$ represent independently a hydrogen atom or a group protecting the amine functional group, provided that $PR_1$ and $PR_2$ are not both (simultaneously) a hydrogen atom, or alternatively $PR_1$ and $PR_2$ together form with the nitrogen atom a cyclic group protecting the amine functional group, Gp represents a leaving group which can be replaced with a fluorine-18 atom, and $\beta$, Y, m and n have the meanings already given above; is brought into contact with a source of fluoride ions F$^-$ labelled with [$^{18}$F], to give a compound of formula (CIb):

$$PR_1-\underset{\underset{PR_2}{|}}{N}-(\beta)_m-(Y)_n-{}^{18}F \quad (CIb)$$

b) the group(s) $PR_1$ and/or $PR_2$ protecting the amine functional group is (are) removed from the compound (Ib) to give a compound of formula (Ic):

$$H_2N-(\beta)_m-(Y)_n{}^{18}F \quad (CIc)$$

c) the compound (CIc) is reacted with a reagent capable of giving a maleimido group from an amino group, so as to obtain the final compound of formula (CI).

The method according to the invention is simple, reliable, easy to carry out and may be easily automated. It comprises only three steps in which one is an extremely simple deprotection step.

The overall duration of the method is short: by way of example, it is generally from 60 to 120 minutes, preferably from 75 to 85 minutes.

The incorporation of the halogen fluorine-18 is carried out in an extremely efficient manner with a high yield, for example 70 to 100%, in particular due to the fact that it is carried out on a heterocyclic group such as pyridine.

The final yield of the entire method for a purified product is extremely high, for example from 15% to 25% and the potential quantities of the "synthon" compound, at the end of synthesis, are also very high.

In the compound (CIa), the groups $PR_1$ and $PR_2$, when they are protective groups, may be any protective group known in organic chemistry. They are preferably chosen from the tert-butoxycarbonyl (BOC) and fluorenylmethoxycarbonyl (FMOC) groups.

When $PR_1$ and $PR_2$ together form with the nitrogen atom of the amine functional group, a group protecting the latter, the protecting group may be for example a phthalimido group.

In the compound (CIa), the Gp group may be any leaving group capable of being replaced by a fluorine-18 atom; Gp is preferably chosen from halogens such as F, Cl, Br, I, mesyl, tosyl and triflate groups, when Y is an alkyl group; and Gp is preferably chosen from halogens, ammonium salts, such as trimethylammoniumtrifluoro-methanesulphonate, and the nitro group, when Y is an aromatic or heterocyclic group.

In step a), the source of fluoride ions labelled with $^{18}$F comprises the said fluoride ions and a counter-ion, chosen from large-sized cations such as rubidium, and tetrabutylammonium, and small-sized cations such as potassium, sodium and lithium, the said small-sized cations being trapped, stabilized, for example by a cryptand or a crown ether, and the like, the said cryptand or crown ether being suitable for the small-sized cation used.

An example of a cryptand is the product KRYPTOFIX® $K_{222}$: (4,7,13,16,21,24-hexaoxa-1,10-diazabicyclo[8.8.8] hexa-cosane) which traps for example the potassium ion.

The counter-ion or cation may be brought in the form of any salt, for example it may be $K_2CO_3$, in the case of potassium.

Step a) is generally carried out in a solvent, which may be any suitable solvent, such as DMSO.

Step a) may be carried out under conditions known to persons skilled in the art, with heating generally at a temperature of 50 to 200° C., for example, 145° C., for a period generally of 1 to 30 minutes, for example of 4 to 6 minutes.

Step b) for removing the group protecting the amine functional group, for deprotection, to give the compound of formula (CIc), where the amino group is free, may be carried out by any known deprotection method. It will be possible for example to bring the compound (CIb) into contact with TFA in $CH_2Cl_2$ for a period generally of 1 to 5, for example of 2 minutes.

It should be noted that TFA is generally used only if the receptor group is removed in an acidic medium, for example when $PR_1$=BOC and $PR_2$=H.

In step c), the reagent capable of giving a maleimido group from an amido group may be any known compound. It may thus be chosen from N-methoxycarbonylmaleimide and succinimide.

Step c) may be carried out under conditions known to persons skilled in the art, for example in a solvent, such as xylene, THF, with heating generally at a temperature of 100 to 200° C., for example of 190° C., for a period of 1 to 20 minutes, for example of 5 minutes.

Step c) may, in another embodiment, also be carried out in a biphasic mixture for example of dioxane and aqueous sodium bicarbonate, at room temperature for a period of 3 to 15 minutes, for example 10 minutes; this embodiment of step c) offers the advantage of giving a better yield and of being carried out at room temperature, without the need to heat the mixture.

The compound of formula (CIa) may correspond to the following formula (CIIa):

$$PR_1-\underset{\underset{PR_2}{|}}{N}-(CH_2)_p-O-\underset{}{\underset{}{\text{pyridine}}}-Gp \quad (CIIa)$$

The compound (CIIa) preferably corresponds to the following formula (CIIb):

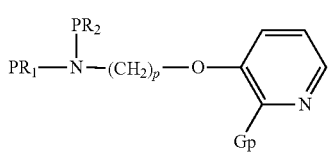
(CIIb)

The compound of formula (CIa) may, in another embodiment, correspond to the following formula (CIIIa):

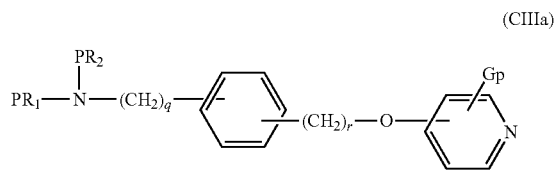
(CIIIa)

The compound (CIIIa) preferably corresponds to the following formula (CIIIb):

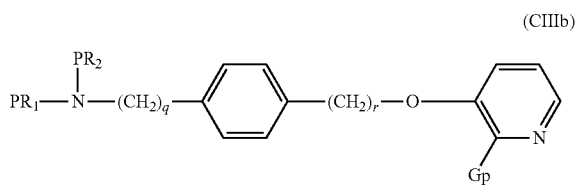
(CIIIb)

The compound of formula (CIa) may, in yet another embodiment, correspond to the following formula (CIVa):

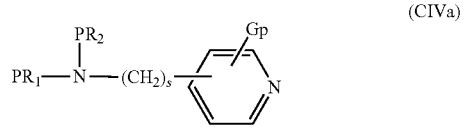
(CIVa)

The compound (CIVa) preferably corresponds to the following formula (CIVb):

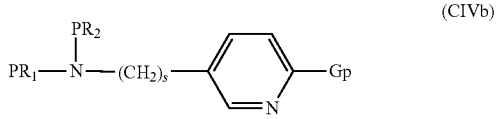
(CIVb)

In another embodiment, the compound of formula (CIa) may correspond to the following formula (CVa):

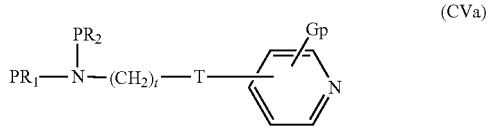
(CVa)

The compound (CVa) preferably corresponds to the following formula (CVb):

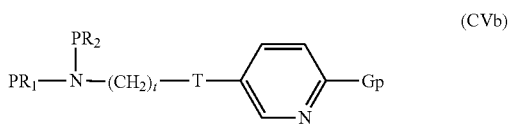
(CVb)

The present invention also relates to a method for synthesizing the peptide labelled with fluorine-18 in accordance with the present invention. This method of synthesis comprises a step of addition of a compound (CI) defined above with a peptide comprising the sequence (PI) defined above. This is indeed an addition reaction carried out between the double bond of the maleimide functional group of the compound (CI) and a free —SH functional group of the peptide, in particular the thiol functional group of a cysteine, of the peptide comprising the peptide sequence (PI). The addition may be carried out directly on a free —SH functional group of the peptide sequence (PI), in particular on the thiol functional group of a cysteine of the peptide sequence, as described above. This addition may be made for example in an acetonitrile/methanol solvent in a ratio of 2:1 by volume, respectively, or in any other appropriate solvent for this type of addition reaction. It will of course be necessary to take care that the solvent used does not affect the peptide (PI) of the invention.

This method therefore has the advantage of being easy to carry out unlike the labeling methods of the prior art.

The coupling will occur, while preserving the activity of the peptide of the present invention, and in general at the ends or at the level of the ends of the peptide of the present invention, on surface residues, or on a part of the peptide sequence different from the sequence (PI) defined above and in particular on the sequence (PII).

The present invention also provides a labelled assemblage having affinity for a phospholipid, comprising at least two peptides comprising the sequence (PI) defined above, which are identical or different, the said peptides being linked to each other, and each or only one of these peptides being labelled by means of a labeling compound (CI) according to the invention. These assemblages may be obtained for example by inserting a flexible peptide linkage, for example polyglycine, between the C-terminal residue of a peptide of the invention and the N-terminal residue of the second peptide and so on depending on the number of peptides joined end to end. This polyglycine linkage may be of formula -(Gly)$_n$-, n being an integer ranging from 1 to 12, for example greater than 4.

These assemblages may also be synthesized by conventional methods of organic chemistry synthesis or protein chemistry, and by genetic recombination in vivo or in vitro, by genetic engineering, and the like, for example by one of the abovementioned methods.

These assemblages are designed in particular to increase the affinity of the peptides of the present invention for the phospholipid, for example for a negatively charged phospholipid.

A labelled peptide or a labelled assemblage of the present invention may be used in two ways which are research and diagnosis, and there are numerous applications.

The pathologies especially targeted by the present invention are: (i) blood clotting disorders, (ii) the phenomena of apoptosis following the action of chemical compounds, physical effects such as ionizing radiation, biological effects such as those linked to the formation or the necrosis of cancer tissues, in addition to normal apoptosis phenomena, (iii) inflammatory pathologies, and (iv) disorders associated with the relationships between the cells and the extracellular matrix and in particular collagen.

The peptides of the present invention have in addition a great advantage compared with the prior art compounds: the reversibility of their folding processes which allows their handling at high temperatures but which are compatible with the chemical stability of the peptides, for the purposes of chemical modifications with the aim of developing molecules which can be used in imagining.

In addition, because of their small size, the peptides of the present invention may be easily combined with other proteins either to form multifunctional chimeric proteins, or to introduce a mechanism for regulation by effectors other than the signalling phospholipids.

According to the invention, the peptides and assemblages according to the invention coupled to the compound (CI) form labeling compounds which can be used for example for in vivo or in vitro diagnosis.

Indeed, the peptides of the present invention may be used for the detection of pathologies involving the appearance of negative charges at the surface of cells and the release of microvesicles into the blood: for example clotting disorders, acute inflammatory pathologies and the like, and apoptosis.

The radioactive halogen is fluorine-18 which is a radio element with a short life span because it allows "in vivo" detection of the localization of the thrombotic regions during all sorts of stroke, in particular of the apoptotic and inflammatory foci using appropriate imaging systems.

The peptides or assemblages labelled with fluorine-18, according to the desired application, may be advantageously packaged in the form of diagnostic kits. Thus, the present invention also provides a diagnostic kit comprising a labelled peptide or assemblage in accordance with the present invention.

The present invention also provides a kit for the analysis and detection of negative charges at the surface of cells, characterized in that it comprises a labelled peptide or assemblage of the present invention.

The present invention also provides a kit for the analysis and detection of microvesicles in the blood, characterized in that it comprises a labelled peptide or assemblage in accordance with the present invention.

The peptides labelled with fluorine-18 according to the invention can therefore be used for the manufacture of a product intended for the detection of centres exposing negatively charged lipids at the surface of cells and/or the release of microvesicles into the blood. As specified above, the detection may be a detection by means of scintigraphic images acquired by positron emission tomography, because the compound (CI) comprises $^{18}$F.

In their application, in the context of "PET", the compounds (CI) and the labelled peptides according to the invention, comprising a fluorine-18 atom, show numerous advantages compared with the compounds with another radioactive halogen, for example iodine.

Indeed, the only positron-emitting iodine isotope is iodine-124, which-could allow PET.

However, it is still produced in small quantities (a few mCi against curies for F-18). It is also difficult to produce. Finally, iodine-124 is not a pure positron emitter (fluorine-18, 97%) and decreases by beta+ emission at 25% only and by electron capture at 75%; it possesses a large number of gamma lines ranging from 0.603 MeV (62%) to 2.75 MeV (1%).

The invention additionally relates to compositions for analysis and detection for example by positron emission tomography (PET), or compositions for diagnosis comprising a peptide labelled with fluorine-18 as described above and a pharmaceutically acceptable vehicle.

Other advantages and characteristics of the present invention will further emerge on reading the illustrative and non-limiting examples which follow, with reference to the figures in the annex.

BRIEF DESCRIPTION OF THE SEQUENCE LISTING

The appended sequences ID No. 1 to ID No. 14 are examples of peptides containing the peptide sequences (PI) and (PII) of the present invention.

In particular, the sequences ID No. 11, ID No. 13 and ID No. 14 are examples of peptides containing the peptide sequence of the present invention in which mutations have been introduced in order to increase the affinity for calcium and phospholipids.

BRIEF DESCRIPTION OF THE FIGURES

In FIG. 1, the top and bottom photos represent different heart sections.

EXAMPLES

Example 1

Synthesis by Genetic Recombination: Expression and Purification of the Peptides of Sequences ID No. 1 to ID No. 12 of the Present Invention The sequences ID No. 1 to ID No. 14 were prepared by overexpression in *E. coli* according to the same protocol as that which has been described by F. Cordier-Ochsenbein et al. in J. Mol. Biol. 279, 1177-1185.

Figure 2:
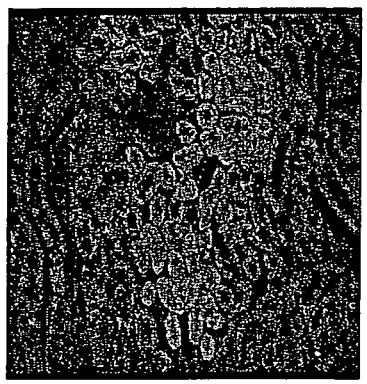
Figure 2:
Figure 2:
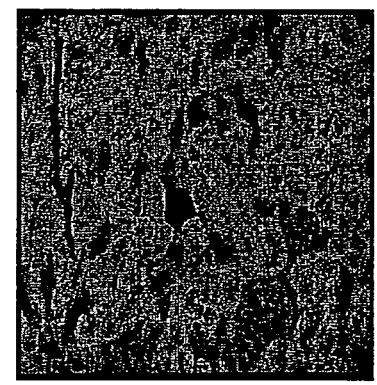
Figure 3:
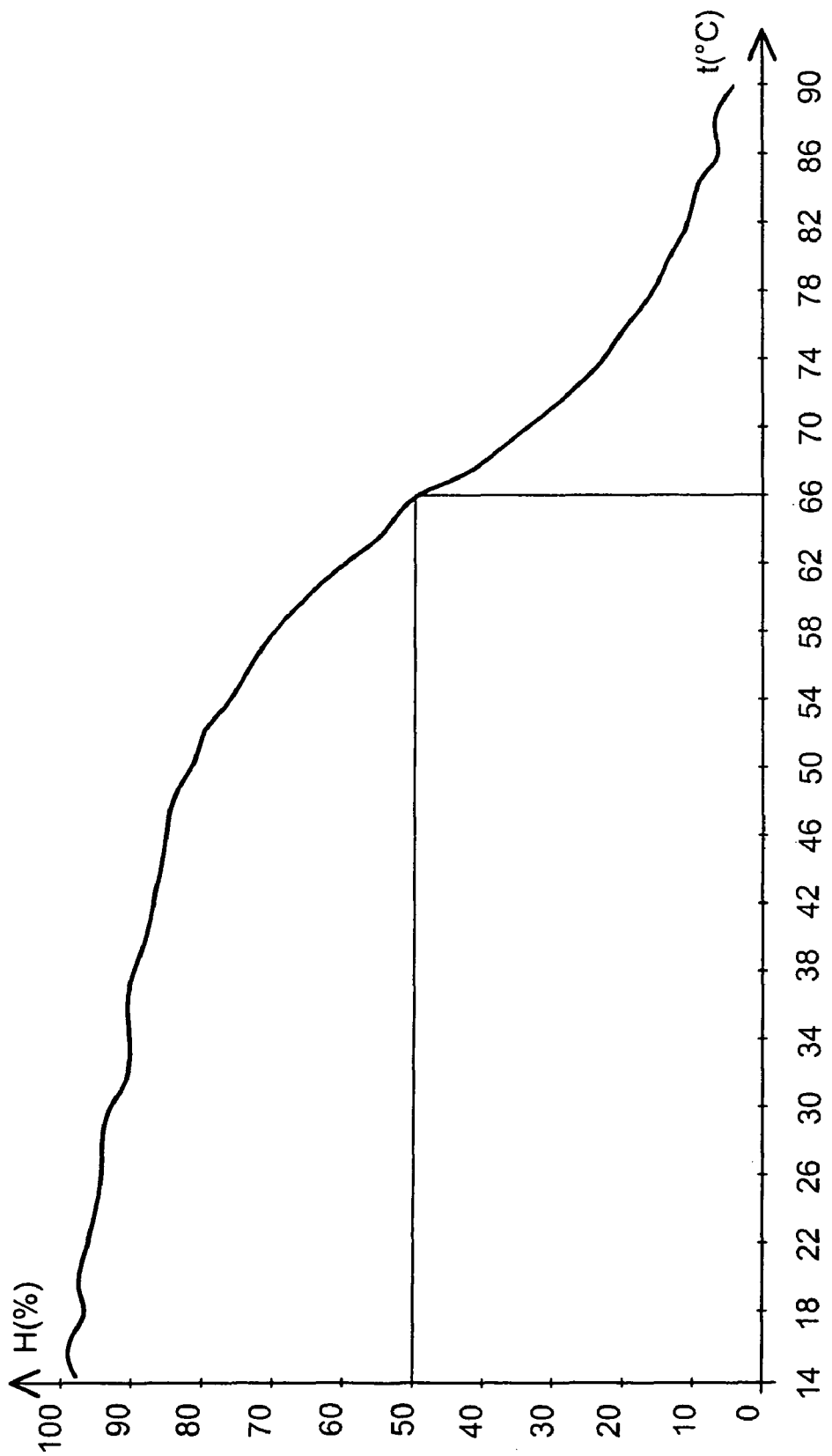
FIG. 3 is a graph which represents the degree of helicity "H" (in %) of a peptide according to the present invention as a function of the temperature "t" in ° C.

The cDNAs of each of these sequences were prepared using a polymerase chain reaction (PCR). They were inserted into the vector pGEX-2T (Smith & Johnson, 1998). FIG. 2 is an image illustrating the insertion of the cDNA into the vector. The absence of PCR-induced mutations was checked by sequencing.

The production of the peptides is carried out using the strain *E. coli* BL21 containing the expression vector described above. After induction with isopropylthiogalactopyranoside (IPTG, 100 µM) to an optical density of 1 to 600 nm, the growth is continued until a plateau is reached, that is to say for about 3 hours. After centrifugation, the bacteria are resuspended in the lysis buffer comprising 50 mM Tris-HCl, pH 8, 10 mM EDTA, 500 mM NaCl, 5% (v/v) glycerol, 1% (v/v) Triton X100, 1 mM dithiothreitol (DTT), 1 mM phenylmethylsulphonyl fluoride (PMSF) and 20 µg/ml of aprotinin.

The purification was carried out in the following manner: after sonication and centrifugation at 10 000 g, the supernatant containing the soluble proteins is incubated with glutathione/agarose beads allowing specific binding of the GST-domain fusion protein to these beads. After washing with a solution containing 1 M NaCl, 50 mM Tris-HCl at pH 8, 70 units of thrombin per liter of culture are added and the sequences are eluted.

The sequences are then purified on a proRPC (trademark) column of the 16/10 type, supplied by the company Pharmacia using an FPLC system and a linear gradient of water of Millipore (trademark) quality containing 0.1% (v/v) of trifluoroacetic acid TFA, and acetonitrile containing 0.1% of TFA. The flow rate is adjusted to 2.5 ml/minute. The sequences are then freeze-dried.

The final yield for each peptide is about 8 mg of sequence per liter of culture.

Example 2

Example of Chemical Synthesis of Peptides of the Present Invention

The peptides of the present invention were manufactured in this example by solid phase chemical synthesis with an Applied Biosystems, mod. 433A automatic peptide synthesizer, and by Fmoc chemistry, which uses the fluorenylmethyloxycarbonyl (Fmoc) group for the temporary protection of the α-amino functional group of the amino acids.

The protecting groups used to prevent side reactions of the side chains of amino acids, in this strategy Fmoc, were tert-butyl ether (tBu) for the Ser, Thr and Tyr residues; tert-butyl ester (OtBu) for Asp, Glu; trityl (Trt) for Gln, Asn, Cys, His; tert-butyloxycarbonyl (Boc) for Lys and 2,2,5,7,8-pentamethylchroman-6-sulphonyl (Pmc) for Arg.

The coupling reaction is carried out with an excess of 10 equivalents of amino acids (1 mmol) relative to the resin (0.1 mmol). The protected amino acid is dissolved in 1 ml of N-methylpyrrolidone (NMP) and 1 ml of a 1M solution of 1-N-hydroxy-7-azabenzotriazole (HOAt) in the solvent NMP. 1 ml of a 1M solution of N,N'-dicyclohexylcarbodiimide (DCC) is then added. After 40 to 50 minutes of activation, the active ester formed is transferred into the reactor which contains the resin. Before this step of transfer and then of coupling, the resin is deprotected of its Fmoc group by a 20% solution of piperidine in NMP. The excess piperidine is removed by washing with NMP after about 5 to 10 minutes.

During the deprotection, the detection of the dibenzofulvenepiperidine adducts at 305 nm makes it possible to monitor the good progress of the synthesis. Indeed, the quantification of the adduct makes it possible to estimate the efficiency of the deprotection of the Fmoc group and thereby of the coupling of the last amino acid incorporated.

The cleavage of the resin and of the protecting groups present on the side chains was carried out simultaneously by treating the peptide linked to the resin with trifluoroacetic acid (TFA). Before carrying out the cleavage, the resin was washed several times with dichloromethane (DCM) and finally dried. The reagent used during the cleavage is an acid mixture containing 81.5% of TFA and the phenol scavengers (5%), water (5%), ethanedithiol (2.5% when the peptide contains a cysteine) and triisopropylsilane (1%). The resin was treated with this mixture for three hours, with stirring and at room temperature, in an amount of 100 ml of solution per gram of resin. The free peptide in solution was recovered by filtration. The peptide was then precipitated and washed in the cold state in diisopropyl ether and then dissolved in 20% acetic acid and freeze-dried.

The peptide recovered after freeze-drying, the crude material from synthesis, is in reduced form, that is to say that the interchain disulphide bridges are not formed.

The peptide is then purified on a proRPC (trademark) column of the 16/10 type, supplied by the company Pharmacia using an FPLC system and a linear gradient of water of Millipore (trademark) quality containing 0.1% by volume of trifluoroacetic acid TFA, and acetonitrile containing 0.1% of TFA. The flow rate is adjusted to 2.5 ml/minute. The peptide is then freeze-dried.

The products obtained were analyzed by mass spectrometry.

Example 3

Stability of the Sequences ID No. 1 to ID No. 14

This example shows that the peptides of the present invention constitute stable folding proteins.

Composition of the Blank (Control):

| | |
|---|---|
| Tris 50 mM, NaCl 150 mM, DTT 1 mM pH 8 | 10 μl |
| $H_2O$ | 990 μl |
| Adjusted to pH 8 | |

Composition of the Sample:

Sample: domain purified in 50 mM Tris buffer containing 150 mM NaCl, pH 8 Approx. concentration: 200 mg.ml.

Domain: 10 μl that is 300 μM final.

$H_2O$: 990 μl pH measured at 7.8.

Hardware and Software Configuration:

Apparatus Jobin Yvon CD6.

Software CD-max

Optical path length of the measurement cuvette: 1 cm.

Figure 1:
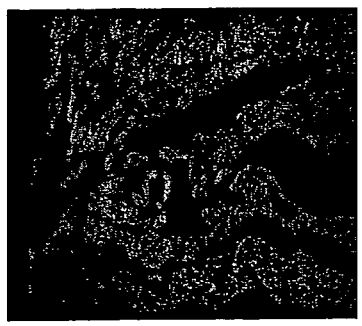
FIGS. 1 and 2 are micrographs obtained from tissue sections of an apoptotic heart (FIG. 1) and of a kidney (FIG. 2), respectively. These sections were obtained, on the one hand, (photos on the left) with AFIM-fluorescein (AFIM-F) peptides of the present invention, on the other hand (photos on the right) with annexin 5-fluorescein (A5-F) (compound of the prior art): fluorescence microscopy, magnification ×40. The photos in the centre were obtained with haematoxylin: visible light microscopy, magnification ×40.
Figure 1:
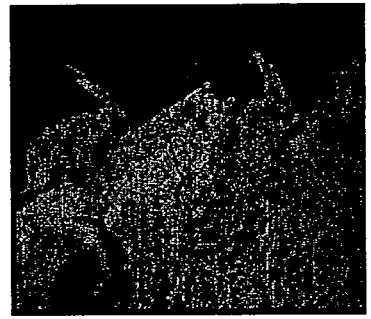
Figure 1:
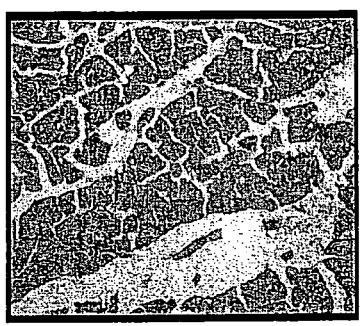
Figure 1:
Figure 1:
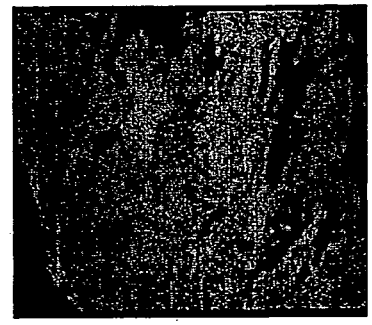

The appended FIG. 1 represents the degree of helicity of AFIM as a function of the temperature as measured with the aid of the circular dichroism signal in far UV at the wavelength of 220 nm.

In this figure, the value of the signal at 14° C. is taken as 100% of the helical content of the peptide. Heat denaturation of the peptide is indeed cooperative and demonstrates that at low temperature and in particular at 37° C., this is a peptide which is suitably folded and exhibiting enhanced stability.

Example 4

Assemblages of Two Peptides of the Present Invention

The method described in Example 1 above is used to synthesize a peptide sequence with the sequence ID No. 1-$(gly)_4$-ID No. 1.

The final yield for the assemblage is about 14 mg/litre of culture.

This assemblage may be labelled with a radioactive halogen according to the present invention, in the same manner as the peptide alone, for example by the method described below.

Example 5

Synthesis of a Labelling Compound of the Present Invention

In this example, there is described the preparation of a labeling compound according to the invention, which is 1-[3-(2-[$^{18}$F]fluoropyridin-3-yloxy)propyl]pyrrole-2,5-dione.

a) Complex K[$^{18}$F]F-K$_{222}$.

In order to recover and recycle the water target [$^{18}$O], it is caused to pass through an anion-exchange resin (AG1×8, from Bio-Rad, 100-200 mesh). The fluoride [$^{18}$F] ion is then eluted from the resin, using 1.0 ml of an aqueous solution of K$_2$CO$_3$ at 4.5 mg/ml.

After addition of 11.0 to 15.0 mg of KRYPTOFIX® K$_{222}$ (4,7,13,16,21,24-hexaoxa-1,10-diazobicyclo[8.8.8]hexacosane), the resulting solution is then gently concentrated to dryness at 145-150° C., under a nitrogen stream for 10 minutes in order to give a pure K[$^{18}$F]F—K$_{222}$ complex, in the form of a white semisolid residue.

b) 1-[3-(2-[$^{18}$F]fluoropyridin-3-yloxy)propyl]pyrrole-2,5-dione

Freshly distilled DMSO (600 μl), containing 4.0 to 6.0 mg of the "nitro" marker precursor (tert-butyl ester of [3-(2-nitropyridin-3-yloxy)propyl]carbamic acid) is added directly to the tube containing the dried K[$^{18}$F]—K$_{222}$ complex. The tube (not sealed) is then placed in a heating block (at 145° C. for 4 minutes). The tube is then cooled using an ice/water bath and the remaining radioactivity is measured.

85% to 95% of the initial activity placed in the container is still present. The reaction mixture obtained, which is dark in color, is then analyzed by radiochromatography. The incorporation yields are calculated from the radiochromatogram by TLC and are defined by the ratio of the surface of the tert-butyl ester of [3-(2-[$^{18}$F]fluoropyridin-3-yloxy)propyl] carbamic acid to the total activity of the $^{18}$F fluorine-18 (SiO$_2$-TLC; eluent: EtOAc; Rf: Rf: 0.75 and Rf: fluoride [$^{18}$F] ion: 0.0). The reaction mixture is diluted with 1 ml of water and transferred into a C18 Sep-pak cartridge (Waters). The tube is rinsed twice with 1 ml of water, which is also transferred and added to the dilute reaction mixture in the cartridge.

The whole is then caused to pass through the cartridge. The cartridge is washed with 3 ml of water and partially dried for 0.5 minute, by sending a nitrogen stream.

The tert-butyl ester derivative of [3-(2-[$^{18}$F]fluoro-pyridin-3-yloxy)propyl]carbamic acid is eluted from the cartridge with 3 ml of dichloromethane in a reaction flask containing 0.1 ml of TFA. Twice 1 ml of dichloromethane are used to wash the cartridge and to completely transfer the [$^{18}$F]-labelled derivative mentioned above (5% of the total quantity of radioactivity involved in the fluorination process remains on the cartridge). The incorporation yield is also confirmed after elution of the Sep-pak by the ratio of the count values for CH$_2$Cl$_2$ to the total radioactivity eluted (DMSO/H$_2$O+ CH$_2$Cl$_2$). The resulting CH$_2$Cl$_2$/TFA solution (50/1, V/V) is concentrated to dryness (at 65-75° C.) under a moderate nitrogen stream for 4 to 6 minutes). The deprotection yield is quantitative: no molecule described above, protected with BOC, can be detected by radiochromatography. The above residue is redissolved in 2 ml of CH$_2$Cl$_2$ and again concentrated to dryness in order to minimize the presence of TFA (at 65-75° C. under a moderate nitrogen stream for 4 to 6 minutes). The residue is then diluted with 0.5 ml of xylene containing 25 mg of N-methoxycarbonylmaleimide. The container is then hermetically closed, heated for 5 minutes at 190° C. (strong reflux), and then cooled for 2 minutes, using an ice-water bath. The reaction mixture is then injected onto a semipreparative HPLC column. Isocratic elution [eluent: heptane/EtOAc: 50/50; flow rate 6.0 ml/minute] which gives pure labelled 1-[3-(2-[$^{18}$F]fluoropyridin-3-yloxy)propyl] pyrrole-2,5-dione, retention time: 7.5 to 8.0 minutes.

Typically, 60 to 70 mCi of pure labelled 1-[3-(2-[$^{18}$F]fluoropyridin-3-yloxy)propyl]pyrrole-2,5-dione may be obtained in 75 to 85 minutes, from 550-650 mCi from an [$^{18}$F]F$^-$ production batch of a cyclotron.

Example 5a

The compound labelled with fluorine-18, 1-[3-(2-[$^{18}$F] fluoropyridin-3-yloxy)propyl]pyrrole-2,5-dione may also be prepared by repeating steps a) and b) of the method described in Example 5, still using, as labeling precursor, the "nitro" compound (tert-butyl ester of [3-(2-nitropyridin-3-yloxy) propyl]carbamic acid), but modifying the final part of the preparation (step c)) in the following manner (variant according to which step c) is carried out in a biphasic mixture of dioxane and aqueous sodium bicarbonate).

After deprotection of the amine functional group (TFA/CH$_2$Cl$_2$), the residue obtained after concentration to dryness is taken up in 0.250 ml of dioxane containing 25 mg of N-methoxycarbonylmaleimide. To this solution, 0.750 ml of a saturated aqueous sodium bicarbonate solution is added, and the preparation is vortexed at room temperature for 10 minutes. The reaction mixture is then diluted with 1 ml of water and transferred onto a C18 Sep-pak cartridge (Waters). The flask is rinsed twice with 1 ml of water, which is also transferred and added to the dilute reaction mixture in the cartridge. Finally, 8 ml of water are again added to the dilute reaction mixture in the cartridge. The whole is then passed through the cartridge. The cartridge is washed with 3 ml of water and partially dried for 0.5 minutes, by sending a nitrogen stream. The derivative labelled with fluorine-18 (1-[3-(2-[$^{18}$F]fluoropyridin-3-yloxy)propyl]pyrrole-2,5-dione) is eluted from the cartridge with 3 ml of dichloromethane in a new empty flask. 1 ml of dichloromethane is used twice to wash the cartridge and to completely transfer the [$^{18}$F]-labelled derivative mentioned above. The solution containing the abovementioned [$^{18}$F]-labelled derivative is concentrated (at 65-75° C., under a moderate nitrogen stream for 3 to 5 minutes) to a volume of about 1 ml and injected onto a semipreparative HPLC column. The purification is identical to that described in Example 5.

Example 5b

The compound labelled with fluorine-18, 1-[3-(2-[$^{18}$F] fluoropyridin-3-yloxy)propyl]pyrrole-2,5-dione may also be prepared by repeating steps a) and b) of the method described in Example 5 or 5 b, but using, as labeling precursor, the compound "trimethylammonium trifluoromethanesulphonate" ([3-(3-tert-butoxycarbonyl-aminopropoxy)pyridine-2-yl]trimethylammonium trifluoro-methanesulphonate).

Example 6

Labelling of a Peptide of the Present Invention with Fluorescein

This example, as well as Example 7 which follows, are intended to demonstrate the efficiency of recognition of apoptotic sites by the peptides of the present invention.

In the examples which follow, the peptide of the present invention is called AFIM-SH. It has a peptide sequence as defined by the sequence (PI). The sequences ID No. 1 to ID No. 14 are tested.

Fluorescein is a molecule which emits a green fluorescence having a wavelength of 525 nm when it is excited at a wavelength of 488 nm. The emission of green light is detected by cameras or photomultipliers. This coupling of AFIM to fluorescein makes it possible to detect the presence of the cells exhibiting PS both in vitro and in vivo in small animals.

According to the present invention, it is possible to label AFIM at the level of the surface residues on any cystein which would be introduced in place of any amino acid present at the surface of AFIM (surface residues) as long as the function for binding to the lipid membranes is not disrupted. AFIM thus modified is designated AFIM-SH below.

The coupling of fluorescein occurs via a maleimide functional group represented below on AFIM by the SH functional group.

The fluorescein is covalently coupled to one or more cysteins of the sequence using a maleimide functional group.

General labelling scheme (scheme I):

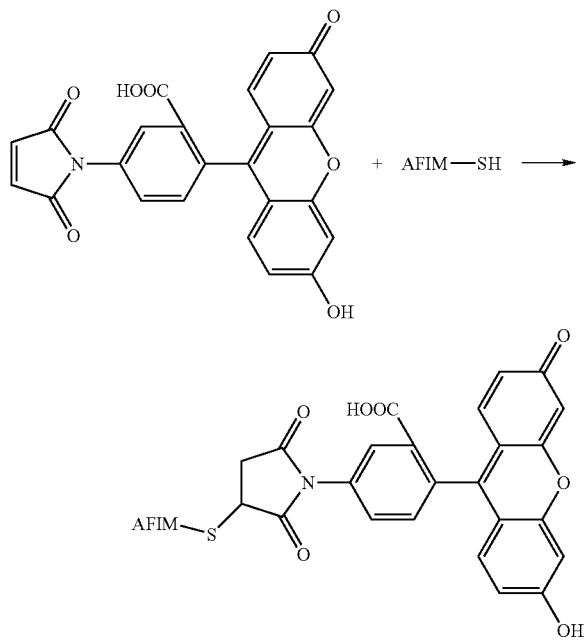

The entire labeling is performed at a temperature of less than 20° C.

AFIM-SH is in solution in Tris buffer. (50 mM), containing NaCl (150 mM), pH=7.4. 5 equivalents of DTT in solution in the same buffer are added to the AFIM-SH solution. The medium is stirred for 30 min.

Protected from light: the fluorescein (5 equivalents of AFIM-SH+2 equivalents of DTT) is weighed and dissolved in DMF, and added to the preceding solution. The whole is stirred, and the reaction is continued for 30 min. Next, the medium is diluted in 150 ml of PBS buffer (20 mM phosphate, 150 mM NaCl), pH=7.4, and ultrafiltered on YM3 (trademark) membrane. The sample is rediluted and ultrafiltered several times, determining the UV spectrum of the filtrate.

When there is no longer any fluorescein in the filtrate (peak at 490 nm), the sample is concentrated to a few ml and stored in the cold at 4° C.

The AFIM-fluorescein products were used to detect apoptotic cells by flow cytometry in vitro, and in animals in vivo in the manner described in Example 7 which follows.

Example 7

Results for Labeling of Apoptotic Cells with the AFIM-fluorescein Products of Example 6

Imaging of apoptotic cardiac cells following a heart attack in rats.

A model of apoptosis in rats is used as described in the article which appeared in *Circulation Res.* 1996, 79, 946-956.

Briefly, four rats (300 g each) were anaesthetized, intubated and ventilated. Myocardial ischaemia was triggered by a transient occlusion of the coronary artery. After 30 minutes of occlusion, the coronary artery was reperfused for one hour.

At the end of the reperfusion period, the AFIM-fluorescein peptides of Example 6 were injected into the jugular vein in an amount of 200 μg of peptide for each of two of the rats in a total volume of 1 ml.

By way of comparison, 200 μg of annexin 5-fluorescein (compounds of the prior art) were injected under the same conditions for each of the other two rats in a total volume of 1 ml.

The rats were sacrificed after 60 minutes.

Five organs were stored for this study: the heart, the lung, the kidney, the liver and the brain. They were washed and rinsed in the presence of formalin. The organs were then dehydrated and impregnated with paraffin for about 12 hours and then 7 μm sections were prepared.

A few sections were stained with haematoxylin. The sections were examined under a fluorescence microscope and the adjacent sections stained with haematoxylin were examined with a visible light microscope. The sections stained with haematoxylin (labelled H1 and H2 respectively in the appended FIGS. 1 and 2) allow visualization of the architecture of the tissues and fluorescence microscopy to detect the labeling with AFIM-fluorescein (AFIM-F) or with annexin 5-fluorescein (A5-F).

The appended FIG. 1 shows the images obtained for the apoptotic heart and the appended FIG. 2 shows the images obtained for the kidney.

FIG. 1 clearly shows the excess of fluorescence corresponding to the accumulation of marker at the level of the apoptotic cells. The contrast is visibly better with AFIM of the present invention than with the prior art annexin 5.

FIG. 2 shows the labeling of the kidney linked to the partial elimination of the products. In the case of AFIM, the glomeruli do not appear to be labelled, only the proximal tubules are partially labelled. On the other hand, in the case of the prior art annexin 5, the entire renal tissue is strongly labelled, which is in agreement with the renal toxicity observed for this protein.

The results obtained in this example demonstrate a high specificity of the peptides of the present invention for the labeling of the cells.

The labeling of the AFIM peptide, for example from ID No. 1 to 10, by fluorescein therefore makes it possible to efficiently detect the phosphatidylserine (PS) present at the outer surface of the cells involved in physiopathological processes such as programmed cell death (apoptosis), blood clotting, inflammatory reaction.

Example 8

Labelling According to the Method of the Present Invention of Peptides Comprising the Sequence (PII) with the Labelling Compound (CI)

In the examples which follow, the peptide of the present invention is called AFIM-SH. It has a peptide sequence as defined by the sequence (PII). The sequences ID No. 1 to ID No. 14 of the appended sequence listing are tested. The labelling compound called synthon $^{18}$F manufactured in Example 5 (or 5a or 5b) is used in this example.

AFIM is coupled, specifically at the level of an SH functional group of the cystein J□ to the synthon $^{18}$F.

The general scheme for the labeling may be summarized in the following manner:

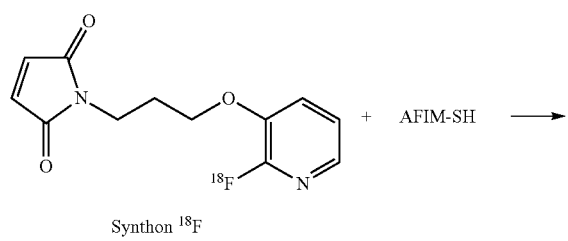 + AFIM-SH →

Synthon $^{18}$F

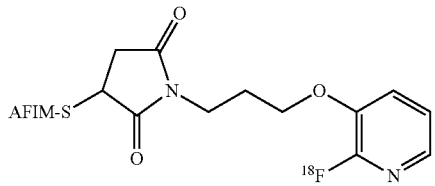

AFIM-SH is in solution in Tris buffer (50 mM) containing NaCl (150 mM), pH=7.4. The synthon $^{18}$F is dissolved in an acetonitrile-methanol (2/1 v/v) mixture, and AFIM-SH is added. The whole is stirred, and the reaction is continued for 3 minutes at room temperature.

The reaction medium is then transferred onto a column of maleimide beads suspended in DMF, and eluted with PBS buffer.

The medium is purified by HPLC on an exclusion gel column, and eluted in PBS buffer (20 mM $KH_2PO_4$, 150 mM NaCl, pH=7.4).

The product, once purified is intravenously injected into rats.

---

The invention claimed is:

1. A peptide labeled with fluorine-18 comprising:
   a peptide sequence (PI) described by SEQ ID NO: 1, 2, 3, 4, 5, 6, 7, 8, 9, 10, 11, 12, 13, or 14,
   wherein said peptide is labeled with a compound (CI) of general formula:

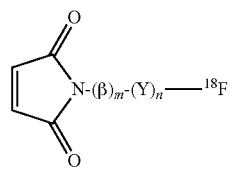

(CI)

in which:
m represents an integer from 0 to 10;
n represents an integer from 0 to 10;
Y represents a group selected from the group consisting of alkyl, imidazolyl, pyrazolyl, benzimidazolyl, pyridinyl, piridazinyl, pyrimidinyl, pyrazinyl, triazinyl, quinolinyl, isoquinolinyl, cinnolinyl, quinazolinyl, quinoxalinyl, and purinyl,
wherein Y may be optionally substituted with one or more substituents selected independently from the group consisting of hydrogen, non-radioactive halogen, phenyl, $C_{1-6}$ alkyl, $C_{1-6}$ alkoxy, aryloxy, amino, mono- or di($C_{1-6}$ alkyl)amino, mono- or di(aryl)amino, thio, $C_{1-6}$ alkylthio, arylthio, formyl, $C_{1-6}$ alkylcarbonyl, arylcarbonyl, carbonyl, $C_{1-6}$ alkoxycarbonyl, aryloxycarbonyl, $C_{1-6}$ alkylaminocarbonyl, arylaminocarbonyl and trifluoromethyl groups;
β represents a radical of formula:

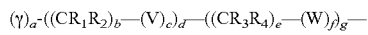

in which:
a, b, c, d, e, f, g each independently represent an integer from 0 to 10;
γ, V and W each independently represent —NR—$_1$, —O—, —S—,

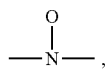

ethynyl, —CR$_1$=CR$_2$, —(C=O)—, —(C=S)—, —C(=NR$_1$)—, —C(=O)O—, —(C=S)S—, —C(=NR$_1$)NR$_2$—, —CR$_1$R$_2$—, —CR$_1$OR$_2$—, —CR$_1$NR$_2$R$_3$—, where R$_1$, R$_2$, R$_3$ and R$_4$ are independently selected from the group consisting of hydrogen, halogen, phenyl, $C_{1-6}$ alkyl, $C_{1-6}$ alkoxy, aryloxy, amino, mono- or di($C_{1-6}$ alkyl)amino, mono- or di(aryl)amino, thio, $C_{1-6}$ alkylthio, arylthio, formyl, $C_{1-6}$ alkylcarbonyl, arylcarbonyl, carbonyl ($C_{1-6}$)alkoxycarbonyl, aryloxycarbonyl, $C_{1-6}$ alkylaminocarbonyl, arylaminocarbonyl, and trifluoromethyl groups;
wherein compound (CI) is bound on an —SH group of said peptide.

2. The peptide labeled with fluorine-18 of claim 1, further comprising at its N-terminal end, the amino acid sequence Gly-Ser-Cys or Gly-Cys-Ser.

3. The peptide labeled with fluorine-18 of claim 1, further comprising at its N-terminal end, the amino acid sequence Gly-Ser-Gly-Cys (SEQ ID NO: 15), Gly-Cys-Gly-Ser (SEQ ID NO: 16) or Gly-Cys-Gly-Cys (SEQ ID NO: 17).

4. The peptide labeled with fluorine-18 according to claim 1, in which the peptide (PI) is labeled directly with the compound (CI) by coupling the maleimide functional group of the compound (CI) with a free —SH functional group of the said peptide (PI).

5. The peptide labeled with fluorine-18 according to claim 1, in which the peptide (PI) is labeled directly with the compound (CI) by coupling the maleimide functional group of the compound (CI) with a free —SH functional group of a cysteine residue of the peptide sequence (PI).

6. The peptide labeled with fluorine-18 according to claim 1, in which, in the compound of formula (CI), n=1, and Y is a 3-pyridinyl group.

7. The peptide labeled with fluorine-18 according to claim 6, in which the compound (CI) corresponds to the following formula (CII):

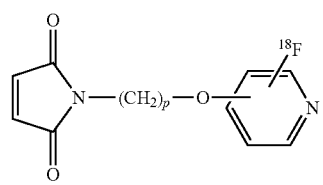

(CII)

in which p is an integer from 1 to 10.

8. A peptide labeled with fluorine-18 according to claim 7, in which the compound of formula (CII) is selected from the group consisting of:
   1-[2-(2-[$^{18}$F]fluoropyridin-3-yloxy)ethyl]pyrrole-2,5-dione;
   1-[4-(2-[$^{18}$F]fluoropyridin-3-yloxy)butyl]pyrrole-2,5-dione;
   1-[5-(2-[$^{18}$F]fluoropyridin-3-yloxy)pentyl]pyrrole-2,5-dione;
   1-[6-(2-[$^{18}$F]fluoropyridin-3-yloxy)hexyl]pyrrole-2,5-dione;
   1-[(2-[$^{18}$F]fluoropyridin-3-yloxy)methyl]pyrrole-2,5-dione;
   1-[3-(2-[$^{18}$F]fluoropyridin-3-yloxy)propyl]pyrrole-2,5-dione.

9. A kit comprising the peptide labeled with fluorine-18 according to claim 1 in form suitable for the analysis and detection of negative charges at the surface of cells.

10. A kit comprising the peptide labeled with fluorine-18 according to claim 1 in form suitable for diagnostic use.

11. A kit comprising the peptide labeled with fluorine-18 according to claim 1 in form suitable for the analysis and detection of microvesicles in blood.

12. A composition comprising a peptide labeled with fluorine-18 according to claim 1 and a pharmaceutically acceptable vehicle.

13. A method for detection or analysis of a phospholipid comprising:
   contacting a phospholipid with the peptide labeled with fluorine-18 according to claim 1,
   and detecting binding, wherein binding indicates the presence of said phospholipid.

14. The method of claim 13, which is positron emission tomography (PET).

15. The peptide labeled with fluorine-18 of claim 1, wherein m and n are not zero.

16. The peptide labeled with fluorine-18 of claim 1, wherein n =1, and Y is pyridinyl.

17. The peptide labeled with fluorine-18 of claim 1, wherein compound (CI) is directly bound via the maleimide group to an —SH group on a cysteine residue in said peptide sequence (PI).

18. A method for detection or analysis of a phospholipid comprising:

contacting a phospholipid with the peptide labeled with fluorine-18 of claim 1, and detecting binding, wherein binding indicates the presence of said phospholipid.

* * * * *